United States Patent [19]

Rhee et al.

[11] Patent Number: 5,308,889
[45] Date of Patent: May 3, 1994

[54] DEHYDRATED COLLAGEN-POLYMER STRINGS

[75] Inventors: Woonza Rhee, Pal Alto; Louis Fries, Los Altos; Ramesh Damani, Mountain View; Kimberly McCullough, Hayward; Frank DeLustro, Belmont, all of Calif.

[73] Assignee: Collagen Corporation, Palo Alto, Calif.

[21] Appl. No.: 984,197

[22] Filed: Dec. 2, 1992

Related U.S. Application Data

[63] Continuation-in-part of Ser. No. 922,541, Jul. 30, 1992, which is a continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^5$ .................. C08G 63/48; C08G 63/91; A61F 2/00
[52] U.S. Cl. ................. 523/113; 523/115; 525/54.1; 424/423; 604/11
[58] Field of Search .............. 525/54.1; 523/113, 115; 424/423; 604/11

[56] References Cited

U.S. PATENT DOCUMENTS 5,162,430 11/1992 Rhee et al. .................. 525/54.1

*Primary Examiner*—Nathan M. Nutter
*Attorney, Agent, or Firm*—Karl Bozicevic

[57] ABSTRACT

Medical articles in the form of strings are formed by covalently binding collagen to pharmaceutically pure, synthetic, hydrophilic polymers via specific types of chemical bonds to provide collagen/polymer conjugate formulations which are extruded to make the strings. The collagen may be recombinantly produced human collagen or collagen extracted from any source, such as a bovine source or human placenta, and purified and can be of various types and may be fibrillar or non-fibrillar. The synthetic hydrophilic polymer may be polyethylene glycol and derivatives thereof having an average molecular weight over a range of from about 100 to about 20,000. The string can be designed to incorporate other components such as fluid, pharmaceutically acceptable carriers to form injectable formulations, and/or biologically active proteins such as growth factors or cytokines. The strings contain large amounts of water when extruded and may then be dehydrated to form relatively solid but flexible strings. The strings can be injected into a living being for the purpose of providing soft tissue augmentation. Once in place, the strings rehydrate and expand in size five fold or more. Aqueous solution can be provided to enhance the rate of rehydration. The strings can also be used to suture wounds which strings can be chemically designed to dissolve in situ.

23 Claims, 5 Drawing Sheets

DEHYDRATED COLLAGEN-POLYMER STRINGS

CROSS-REFERENCES

This application is a continuation-in-part of copending U.S. application Ser. No. 07/922,541 filed Jul. 30, 1992, which is a continuation-in-part of U.S. application Ser. No. 07/433,441 filed Nov. 14, 1989 (now U.S. Pat. No. 5,162,430 issued Nov. 10, 1992), which is a continuation-in-part of U.S. application Ser. No. 07/274,071 filed Nov. 21, 1988 (abandoned), all of which are incorporated herein by reference in full and to which applications we claim priority under 35 USC §120.

FIELD OF THE INVENTION

This invention relates to medical articles useful for soft tissue augmentation and as sutures and specifically to articles in the form of strings comprising pharmaceutically acceptable, non-immunogenic compositions produced by conjugating collagen to a synthetic hydrophilic polymer such as polyethylene glycol (PEG). The strings can be produced by extrusion, dehydrated and delivered through a fine gauge needle to a soft tissue site in need of augmentation.

BACKGROUND OF THE INVENTION

Collagen is the major protein component of bone, cartilage, skin, and connective tissue in animals. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence -Gly-X-Y-, where X and Y are often proline or hydroxyproline, bounded at each end by the "telopeptide" regions, which constitute less than about 5% of the molecule. The telopeptide regions of the collagen chains are typically responsible for the cross-linking between chains, and for the immunogenicity of the protein. Collagen occurs in several "types", having differing physical properties. The most abundant types are Types I, II and III.

Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Collagen may be denatured by boiling, which produces the familiar product gelatin.

Daniels et al, U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm ® collagen implant.

Luck et al, U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase ®. The enzyme digestion removes the telopeptide portions of the collagen molecules, providing "atelopeptide" collagen in solution. The atelopeptide CIS so produced is substantially non-immunogenic, and is also substantially non-cross-linked due to loss of the primary crosslinking regions. The CIS may then be precipitated by dialysis in a moderate shear environment to produce collagen fibers which resemble native collagen fibers. The precipitated, reconstituted fibers may additionally be cross-linked using a chemical agent (for example aldehydes such as formaldehyde and glutaraldehyde), or using heat or radiation. The resulting products are suitable for use in medical implants due to their biocompatibility and reduced immunogenicity.

Wallace et al, U.S. Pat. No. 4,424,208, disclosed an improved collagen formulation suitable for use in soft tissue augmentation. Wallace's formulation comprises reconstituted fibrillar atelopeptide collagen (for example, Zyderm ® collagen) in combination with particulate, crosslinked atelopeptide collagen dispersed in an aqueous medium. The addition of particulate crosslinked collagen improves the implant's persistence, or ability to resist shrinkage following implantation.

Smestad et al, U.S. Pat. No. 4,582,640, disclosed a glutaraldehyde crosslinked atelopeptide CIS preparation (GAX) suitable for use in medical implants. The collagen is crosslinked under conditions favoring intrafiber bonding rather than interfiber bonding, and provides a product with higher persistence than non-cross-linked atelopeptide collagen, and is commercially available from Collagen Corporation under the trademark Zyplast ® Implant.

Nguyen et al, U.S. Pat. No. 4,642,117, disclosed a method for reducing the viscosity of atelopeptide CIS by mechanical shearing. Reconstituted collagen fibers are passed through a fine-mesh screen until viscosity is reduced to a practical level for injection.

Nathan et al, U.S. Pat. No. 4,563,350, disclosed osteoinductive bone repair compositions comprising an osteoinductive factor, at least 5% nonreconstituted (afibrillar) collagen, and the remainder reconstituted collagen and/or mineral powder (e.g., hydroxyapatite). CIS may be used for the nonreconstituted collagen, and Zyderm ® collagen implant (ZCI) is preferred for the reconstituted collagen component. The material is implanted in bone defects or fractures to speed ingrowth of osteoclasts and promote new bone growth.

Chu, U.S. Pat. No. 4,557,764, disclosed a "second nucleation" collagen precipitate which exhibits a desirable malleability and putty-like consistency. Collagen is provided in solution (e.g., at 2-4 mg/mL), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu, U.S. Pat. No. 4,689,399, disclosed a collagen membrane preparation, which is prepared by compressing and drying a collagen gel. The resulting product has high tensile strength.

J. A. M. Ramshaw et al, *Anal Biochem* (1984) 141:361–65, and PCT application WO87/04078 disclosed the precipitation of bovine collagen (types I, II, and III) from aqueous PEG solutions, where there is no binding between collagen and PEG.

Werner, U.S. Pat. No. 4,357,274, disclosed a method for improving the durability of sclero protein (e.g., brain meninges) by soaking the degreased tissue in $H_2O_2$ or PEG for several hours prior to lyophilizing. The resulting modified whole tissue exhibits increased persistence.

Hiroyoshi, U.S. Pat. No. 4,678,468, disclosed the preparation of polysiloxane polymers having an interpenetrating network of water-soluble polymer dispersed within. The water-soluble polymer may be a collagen derivative, and the polymer may additionally include heparin. The polymers are shaped into artificial blood vessel grafts, and are designed to prevent clotting.

Other patents disclose the use of collagen preparations with bone fragments or minerals, For example, Miyata et al, U.S. Pat. No. 4,314,380 disclosed a bone implant prepared by baking animal bone segments, and soaking the baked segments in a solution of atelopeptide collagen. Deibig et al, U.S. Pat. No. 4,192,021 disclosed an implant material which comprises powdered calcium phosphate in a pasty formulation with a biodegradable polymer (which may be collagen). Commonly-owned copending U.S. patent application Ser. No. 855,004, filed Apr. 22, 1986, disclosed a particularly effective bone repair material comprising autologous bone marrow, collagen, and particulate calcium phosphate in a solid, malleable formulation.

There are several references in the art to proteins modified by covalent conjugation to polymers, to alter the solubility, antigenicity and biological clearance of the protein. For example, U.S. Pat. No. 4,261,973 disclosed the conjugation of several allergans to PEG or PPG (polypropylene glycol) to reduce the proteins' immunogenicity. U.S. Pat. No. 4,301,144 disclosed the conjugation of hemoglobin with PEG and other polymers to increase the protein's oxygen carrying capability. EPO 98,110 disclosed coupling an enzyme or interferon to a polyoxyethylene-polyoxypropylene (POE-POP) block polymer increases the protein's halflife in serum. U.S. Pat. No. 4,179,337, disclosed conjugating hydrophilic enzymes and insulin to PEG or PPG to reduce immunogenicity. Davis et al, *Lancet* (1981) 2:281-83 disclosed the enzyme uricase modified by conjugation with PEG to provide uric acid metabolism in serum having a long halflife and low immunogenicity. Nishida et al, *J Pharm Pharmacol* (1984) 36:354-55 disclosed PEG-uricase conjugates administered orally to chickens, demonstrating decreased serum levels of uric acid. Inada et al, *Biochem & Biophys Res Comm* (1984) 122:845-50 disclosed lipoprotein lipase conjugation with PEG to render it soluble in organic solvents. Takahashi et al, *Biochem & Biophys Res Comm* (1984) 121:261-65 disclosed HRP conjugated with PEG to render the enzyme soluble in benzene. Abuchowski et al, *Cancer Biochem Biophys* (1984) 7:175-86 disclosed that enzymes such as asparaginase, catalase, uricase, arginase, trypsin, superoxide dismutase, adenosine deaminase, phenylalanine ammonia-lyase, and the like, conjugated with PEG exhibit longer half-lives in serum and decreased immunogenicity. However, these references are essentially concerned with modifying the solubility and biological characteristics of proteins administered in low concentrations in aqueous solution.

M. Chvapil et al, *J Biomed Mater Res* (1969) 3:315-32 disclosed a composition prepared from collagen sponge and a crosslinked ethylene glycol monomethacrylate-ethylene glycol dimethacrylate hydrogel. The collagen sponge was prepared by lyophilizing an aqueous mixture of bovine hide collagen and methylglyoxal (a tanning agent). The sponge-hydrogel composition was prepared by polymerizing ethylene glycol monomethacrylate and ethylene glycol dimethacrylate in the sponge.

SUMMARY OF THE INVENTION

Medical articles in the form of strings, i.e., elongated cylinders are provided by extruding a formable composition through any suitable orifice including a needle or the nozzle of any suitable extrusion device and dehydrating the extruded string. The extruded composition is a pharmaceutically acceptable non-immunogenic composition formed by covalently binding atelopeptide collagen to pharmaceutically pure, synthetic, hydrophilic polymers via specific types of chemical bonds to provide collagen/polymer conjugates. Any type of collagen can be used including recombinantly produced human collagen and extracted and purified collagen including atelopeptide collagen which can be type I, type II or type III collagen. The collagen can be extracted from various sources such as bovine hide and human placenta and may be fibrillar or non-fibrillar. The synthetic hydrophilic polymer may be polyethylene glycol and derivatives thereof having a weight average molecular weight over a range of from about 100 to about 20,000. The compositions may include other components such as pharmaceutically acceptable fluid carriers (which are preferably nonaqueous) to aid in delivery to the soft tissue site and/or biologically active proteins such as cytokines which may be incorporated in the string. The collagen-polymer conjugates of the invention generally contain large amounts of water when formed. The extruded strings are dehydrated, resulting in a flexible string. The dehydrated flexible string can be injected into a living being for the purpose of soft tissue augmentation. Once in place, the string will rehydrate and expand in size by several fold, e.g., in the range of from above 2 to 7 times its dehydrated volume. Dehydrated strings can also be woven into materials which can be used as implants in order to strengthen or act as bandages for tendons or ligaments. Such woven material can also act as blood vessel grafts, vascular stents or nerve growth tubes, i.e., tubes produced by woven strings are wrapped around a broken or damaged nerve. In that the materials are woven when dehydrated, the strings will expand on rehydration providing an impermeable barrier in situ. Further, the collagen/polymer conjugates are not thrombogenic making them ideal for use in connection with blood vessels.

A primary object of the invention is to provide dehydrated strings or threads comprising collagen-polymer conjugates formed by covalently binding polymers such as polyethylene glycol to collagen.

Another object of the invention is to provide a method of tissue augmentation comprising forming strings comprising collagen-polymer conjugates, dehydrating the strings and injecting the string into the site of augmentation after which the string will rehydrate and expand in size.

Still another object is to use the dehydrated strings to produce woven or knitted materials including implantable bandages, blood vessel grafts, vascular stents, nerve growth tubes, artificial ligaments and artificial tendons.

An advantage of the present invention is that the collagen-polymer conjugates have a high degree of stability over long periods of time under physiological conditions.

Still another advantage of the invention is that the strings can be extruded and thereby produced in a discrete unit and thereby more readily removed if necessary as compared with standard injectable compositions.

Yet another advantage of the invention is that materials comprised of the polymer/collagen conjugates are not thrombogenic thus making them preferred materials for use in connection with the cardiovascular system.

A feature of the invention is that the conjugates can be formed using a range of different molecular weight polymers in order to adjust physical characteristics of the strings such as flexibility and amount of expansion on rehydration.

Another feature of the invention is that the strings may be formed having a variety of different cross-sections including circular, oval, and rectangular, as well as a variety of different shapes, such as straight and coils, and the cross-section and shapes may be varied depending on the method of drying used and the intended end use.

Still another feature of the invention is that by weaving materials with dehydrated strings into a tight weave, the material becomes an impermeable barrier in situ when the strings are rehydrated and expand in size.

Another advantage of the present invention is that the strings comprising collagen-polymer conjugate compositions generate a decreased immune reaction as compared with articles comprised of conventional pharmaceutically acceptable collagen compositions and collagen compositions crosslinked by other means, such as heat, irradiation, or glutaraldehyde treatment.

Other advantages and features of the present invention is that the strings are compact and easy to handle in their dehydrated form, allowing them to be readily stored, transported and inserted into a patient for soft tissue augmentation.

Other features of the present invention include the ability to formulate the compositions used to form the strings with pharmaceutically active molecules such as cytokines in order to improve the activity and available half-life of such cytokines under physiological conditions.

Another feature of the present invention is that the collagen may be bound to the polymer by means of a covalent ether linkage for long term stability or by an ester linkage when it is desirable to have the string degrade over time.

These and other objects, advantages and features of the present invention will become apparent to those persons skilled in the art upon reading the details of the structure, synthesis, and usage of the collagen-polymer conjugates as more fully set forth below, reference being made to the attached figures and included specific examples and formulations forming a part hereof.

DETAILED DESCRIPTION OF PREFERRED EMBODIMENTS OF THE INVENTION

Figure 1:
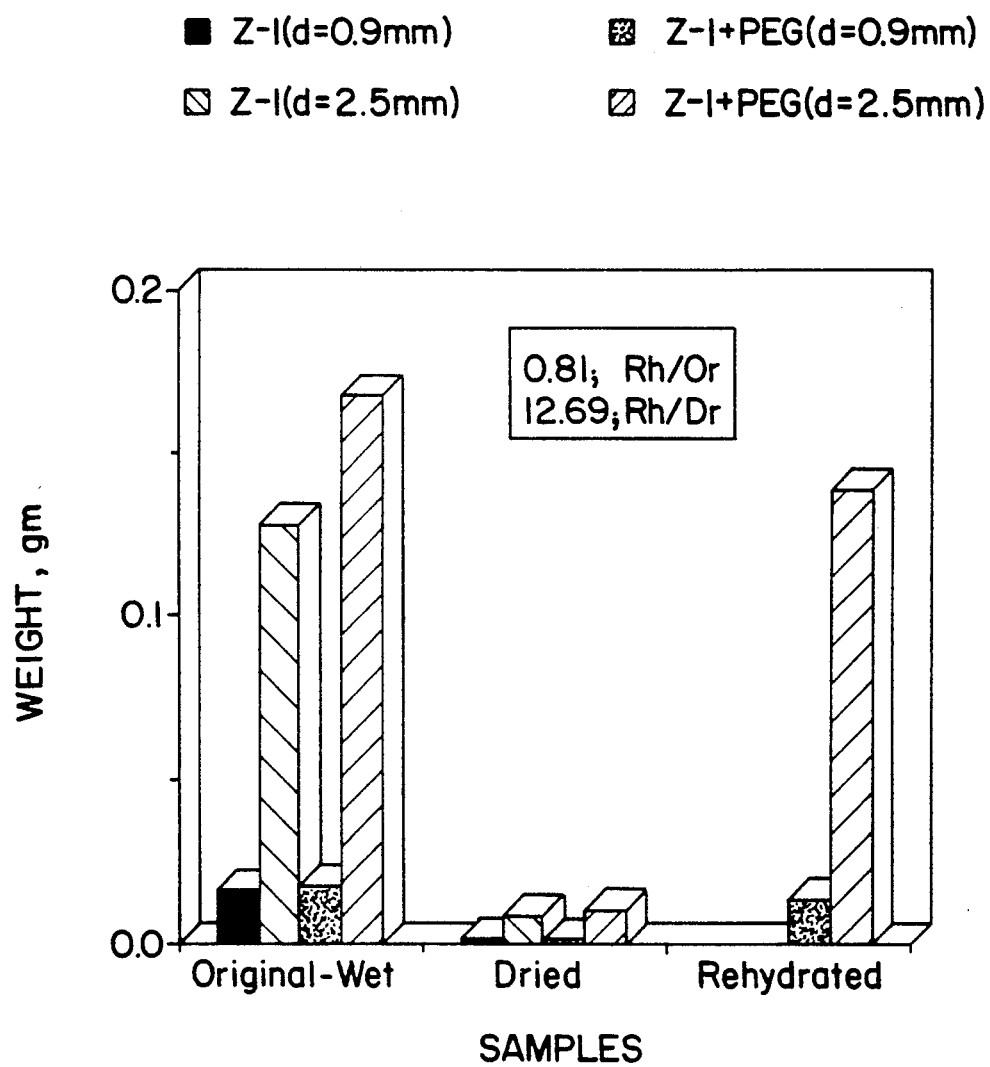
FIG. 1 is a graph which shows the weight in grams of the original strings in their hydrated form, dried and in a rehydrated state.
Figure 2:
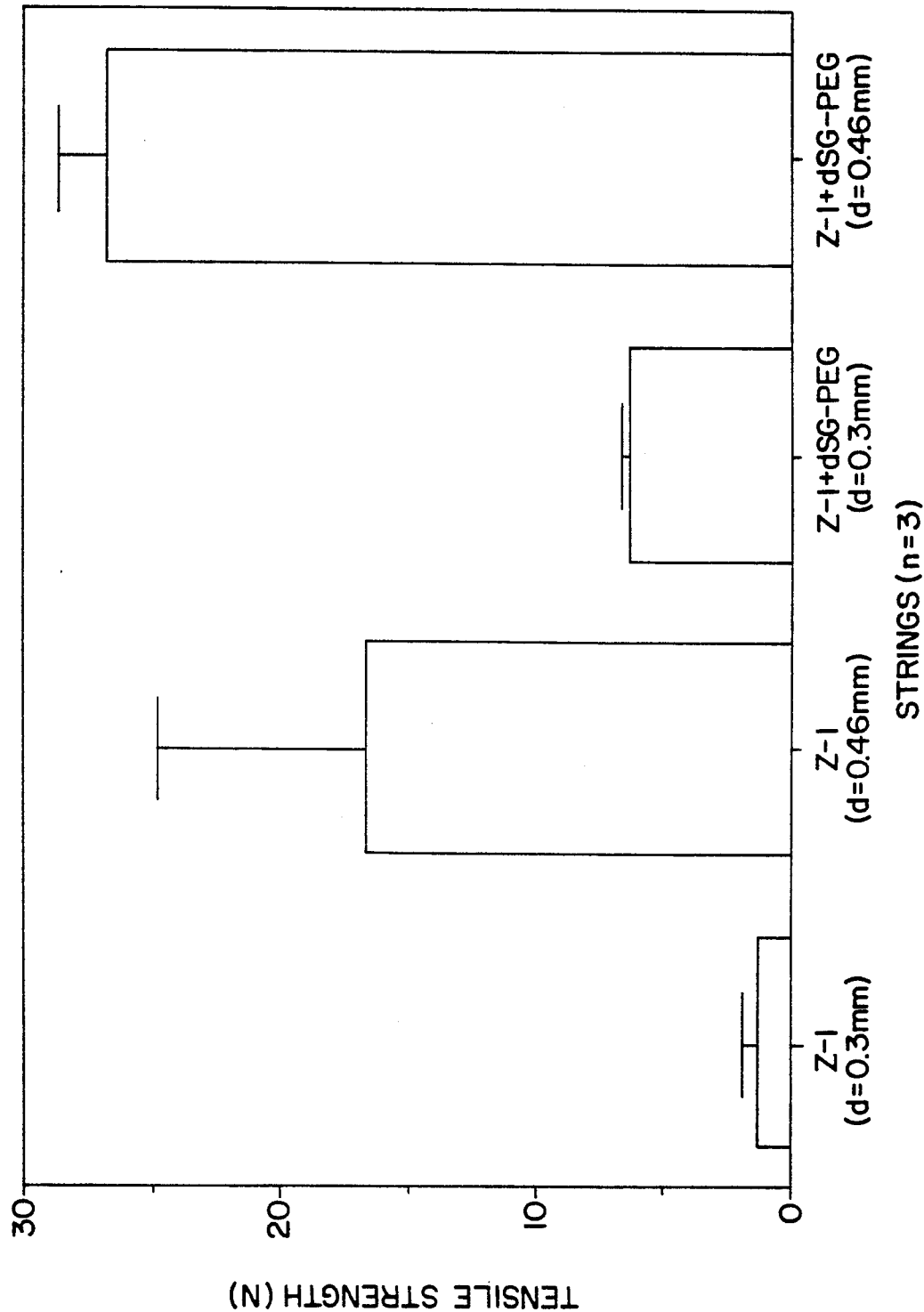
FIG. 2 is a graph which shows the tensile strength of different strings.
Figure 3:
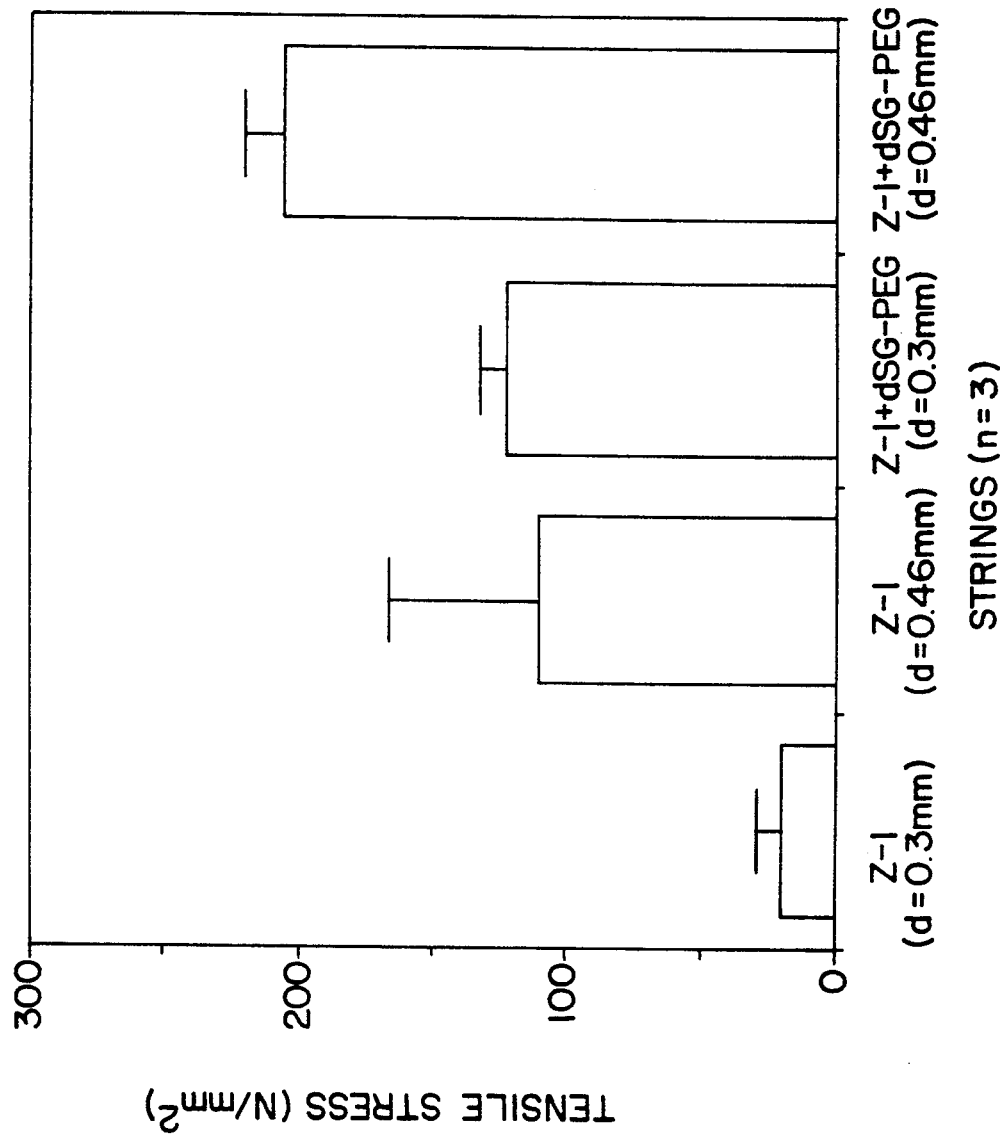
FIG. 3 is a graph which demonstrates the tensile stress which different strings can withstand.
Figure 4:
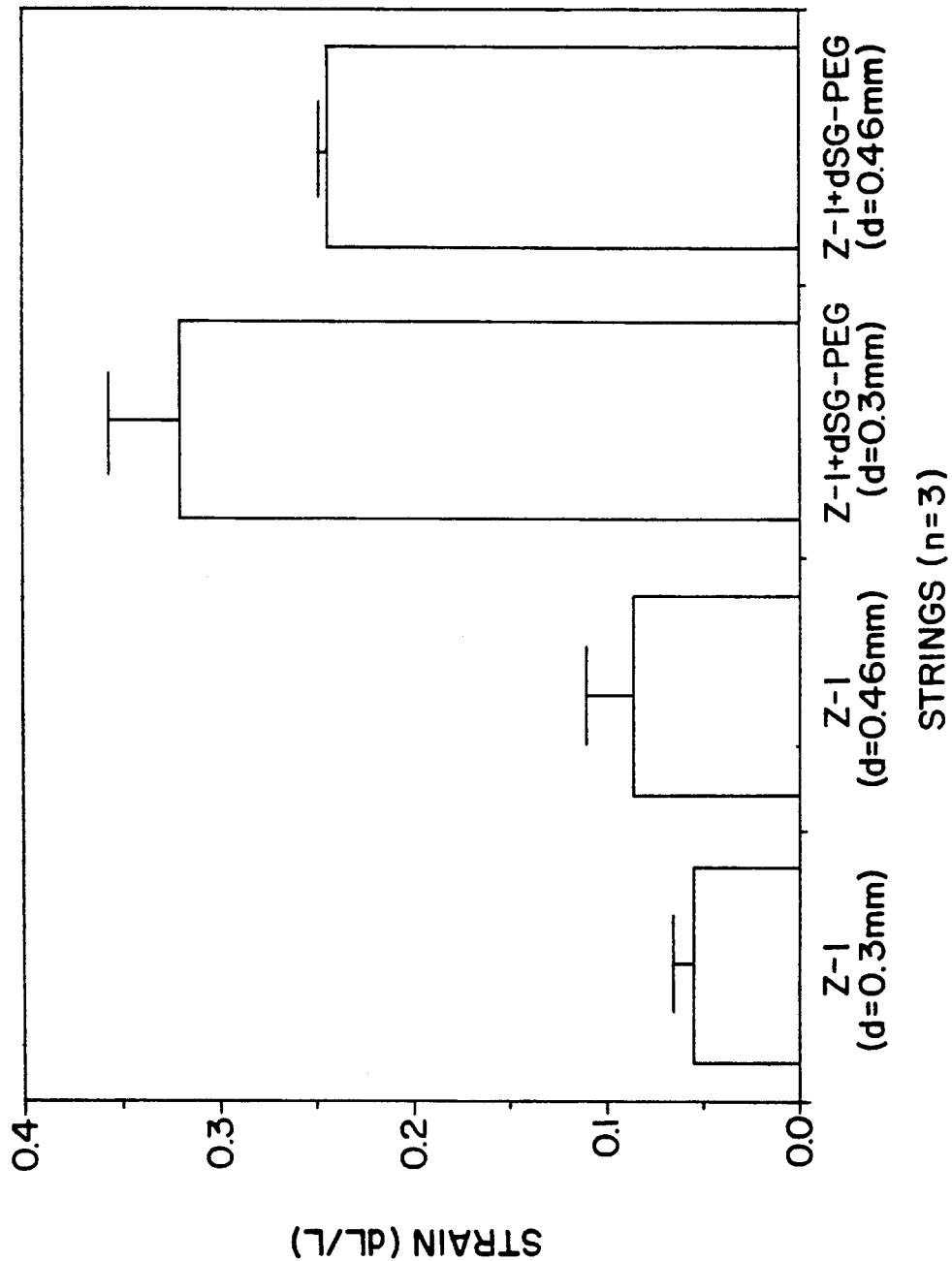
FIG. 4 is a graph which shows the amount of strain which different strings can withstand.
Figure 5:
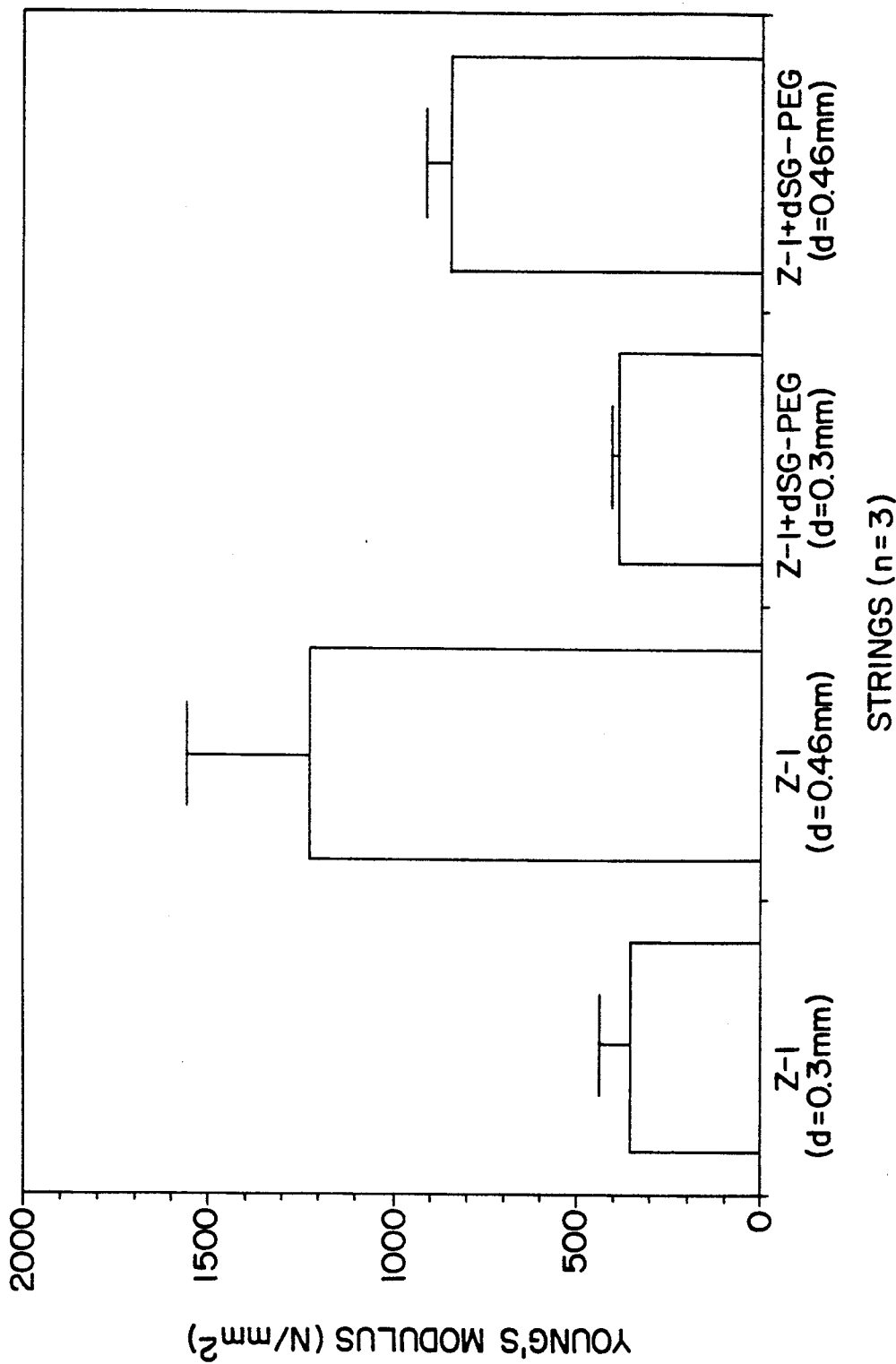
FIG. 5 is a graph showing the Young's Modulus of different strings.

Before the dried collagen-polymer strings and processes for making and using such are described, it is to be understood that this invention is not limited to the particular extruded strings, conjugates, processes or methods described as such may, of course, vary. It is also to be understood that the terminology used herein is for the purpose of describing particular embodiments only, and is not intended to be limiting as the scope of the present invention will be limited only by the appended claims.

It must be noted that, as used in this specification and the appended claims, the singular forms "a", "an" and "the" include plural referents unless the context clearly dictates otherwise. Thus, for example, reference to "a string" includes one or more strings, reference to "an amino group" includes one or more different types of amino groups known to those skilled in the art and reference to "the collagen" includes mixtures of different types of collagens and so forth.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred methods and materials are described below. All publications mentioned herein are incorporated herein by reference. Further, specific terminology of particular importance to the description of the present invention is defined below.

A. DEFINITIONS

The term "collagen" as used herein refers to all forms of collagen, including those which have been recombinantly produced, extracted, processed or otherwise modified. Preferred collagens are non-immunogenic and, if extracted from animals, are treated to remove the immunogenic telopeptide regions ("atelopeptide collagen"), are soluble, and may be in the fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may be conjugated with polymers as described herein to form particularly rigid compositions. Collagen crosslinked using glutaraldehyde or other (nonpolymer) linking agents is referred to herein as "GAX", while collagen crosslinked using heat and/or radiation is termed "HRX." Collagen used in connection with the preferred embodiments of the invention is in a pharmaceutically pure form such that it can be incorporated into a human body for the intended purpose.

The term "synthetic hydrophilic polymer" as used herein refers to a synthetic polymer having an average molecular weight and composition which renders the polymer essentially water-soluble. Preferred polymers are highly pure or are purified to a highly pure state such that the polymer is or is treated to become pharmaceutically pure. Most hydrophilic polymers can be rendered water-soluble by incorporating a sufficient number of oxygen (or less frequently nitrogen) atoms available for forming hydrogen bonds in aqueous solutions. Preferred polymers are hydrophilic but not soluble. Preferred hydrophilic polymers used herein include polyethylene glycol, polyoxyethylene, polymethylene glycol, polytrimethylene glycols, polyvinylpyrrolidones, and derivatives thereof. The polymers can be linear or multiply branched and will not be substantially crosslinked. Other suitable polymers include polyoxyethylene-polyoxypropylene block polymers and copolymers. Polyoxyethylene-polyoxypropylene block polymers having an ethylene diamine nucleus (and thus having four ends) are also available and may be used in the practice of the invention. Naturally occurring and/or biologically active polymers such as proteins, starch, cellulose, heparin, and the like are expressly excluded from the scope of this definition although the invention includes polymer mixtures with naturally occurring polymers therein, i.e, the natural polymer is not used to form the basic collagen/polymer conjugate but might be mixed with or bond to the conjugate after it is formed. All suitable polymers will be non-toxic, non-inflammatory and non-immunogenic when used to form strings, and will preferably be essentially nondegradable in vivo over a period of at least several months. The hydrophilic polymer may increase the hydrophilicity of the collagen, but does not render it water-soluble. Presently preferred hydrophilic polymers are mono-, di-, and multifunctional polyethylene glycols (PEG). Monofunctional PEG has only one reactive hydroxy group, while difunctional PEG has reactive groups at each end. Monofunctional PEG preferably has a weight average molecular weight between about 100 and about 15,000, more preferably between about 200 and about 8,000, and most preferably about 4,000. Difunctional PEG preferably has a molecular weight of about 400 to about 40,000, more preferably about 3,000 to about 10,000. Multifunctional PEG preferably has a molecular weight between about 3,000 and 100,000.

PEG can be rendered monofunctional by forming an alkylene ether at one end. The alkylene ether may be any suitable alkoxy radical having 1-6 carbon atoms, for example, methoxy, ethoxy, propoxy, 2-propoxy, butoxy, hexyloxy, and the like. Methoxy is presently preferred. Difunctional PEG is provided by allowing a reactive hydroxy group at each end of the linear molecule. The reactive groups are preferably at the ends of the polymer, but may be provided along the length thereof. Polyfunctional molecules are capable of crosslinking the compositions of the invention, and may be used to attach cytokines or growth factors to collagen which can diffuse out of the strings.

The term "chemically conjugated" as used herein means attached through a covalent chemical bond. In the practice of the invention, a synthetic hydrophilic polymer and collagen may be chemically conjugated by using a linking radical, so that the polymer and collagen are each bound to the radical, but not directly to each other. The term "collagen-polymer" refers to collagen chemically conjugated to a synthetic hydrophilic polymer, within the meaning of this invention. Thus, "collagen-PEG" (or "PEG-collagen") denotes a composition of the invention wherein collagen is chemically conjugated to PEG. "Collagen-dPEG" refers to collagen chemically conjugated to difunctional PEG, wherein the collagen molecules are typically crosslinked. "Crosslinked collagen" refers to collagen in which collagen molecules are linked by covalent bonds with polyfunctional (including difunctional) polymers. Terms such as "GAX-dPEG" and "HRX-dPEG" indicate collagen crosslinked by both a difunctional hydrophilic polymer and a crosslinking agent such as glutaraldehyde or heat. The polymer may be "chemically conjugated" to the collagen by means of a number of different types of chemical linkages. For example, the conjugation can be via an ester or urethane linkage, but is more preferably by means of an ether linkage. An ether linkage is preferred in that it can be formed without the use of toxic chemicals and is not readily susceptible to hydrolysis in vivo. Although the collagen/polymer conjugates used in the invention and can be produced by a variety of different procedures as described herein, they are generally synthesized by one of three general procedures which includes: (1) reacting an activated or reactive group on the collagen with a group on the polymer so as to form a covalent bond; (2) reacting an activated or reactive group on the polymer with a group on the collagen so as to form a covalent bond; or (3) reacting an activated or reactive group on a first position of a linking group with a group on the collagen and reacting a reactive or activated group at a second position on the linking group with a group on the polymer so as to form covalent bonds. Variations and combinations of all or any of (1), (2) or (3) may be used.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "available lysine residue" as used herein refers to lysine side chains exposed on the outer surface of collagen molecules, which are positioned in a manner to allow reaction with activated PEG. The number of available lysine residues may be determined by reaction with sodium 2,4,6-trinitrobenzenesulfonate (TNBS).

The terms "treat" and "treatment" as used herein refer to augmentation, repair, prevention, or alleviation of defects, particularly defects due to loss or absence of soft tissue or soft tissue support. Additionally, "treat" and "treatment" also refer to the use of strings as sutures which aid in wound healing, particularly when combined with a biologically active protein coupled to the collagen-polymer composition. Accordingly, treatment of soft tissue includes augmentation of soft tissue, for example implantation of strings of the invention to restore normal or desirable dermal contours, as in the removal of dermal creases or furrows, or as in the replacement of subcutaneous fat in maxillary areas where the fat is lost due to aging, or in the augmentation of submucosal tissue such as the urinary or lower esophageal sphincters.

The terms "cytokine" and "growth factor" are used to describe biologically active molecules and active peptides (which may be naturally occurring or synthetic) which aid in healing or regrowth of normal tissue. The function of cytokines and growth factors is two-fold: 1) they can incite local cells to produce new collagen or tissue, or 2) they can attract cells to the site in need of correction. As such, cytokines and growth factors serve to encourage "biological anchoring" of the collagen implant within the host tissue. As previously described, the cytokines and growth factors can either be admixed with the collagen-polymer conjugate or chemically coupled to the conjugate. For example, one may incorporate cytokines such as interferons (IFN), tumor necrosis factors (TNF), interleukins, colony stimulating factors (CSFs), or growth factors such as epidermal growth factor (EGF), transforming growth factor (TGF) alpha, TGF-$\beta$ (including any combination of TGF-$\beta$s), TGF-$\beta$1, TGF-$\beta$2, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, erythropoietin (EPO), nerve growth factor (NGF), bone morphogenic protein (BMP), osteogenic factors, and the like. Incorporation of cytokines, growth factors, and appropriate combinations of cytokines and growth factors can facilitate regrowth when the strings are used in the treatment of wounds. Furthermore, one may chemically link the cytokines or growth factors to the collagen-polymer composition by employing a suitable amount of multifunctional polymer molecules during synthesis. The cytokines may then be attached to the free polymer ends by the same method used to attach PEG to collagen, or by any other suitable method. By tethering cytokines to the string, the effective amount of cytokine is substantially reduced. Strings which incorporate cytokines may provide effective controlled-release drug delivery. By varying the chemical linkage between the collagen and the synthetic polymer, it is possible to vary the effect with respect to the release of the cytokine. For example, when an "ester" linkage is used, the linkage is more easily broken under physiological conditions, allowing for sustained release of the growth factor from the matrix. Such hydrolizable ester bonds may be used to provide sutures which dissolve in situ. However, when an "ether" linkage is used, the bonds are not easily broken and the cytokine or growth factor will remain in place for longer periods of time with its active sites exposed providing a biological effect on the natural substrate for the active site of the protein. It is possible to include a mixture of conjugates with different linkages so as to obtain variations in the effect with respect to the release of the cytokine, i.e., the sustained release effect can be modified to obtain the desired rate of release and/or the rate at which the sutures dissolve can be adjusted.

The term "effective amount" refers to the amount of composition required in order to obtain the effect desired. Thus, a "tissue growth-promoting amount" of a composition containing a growth factor refers to the amount of growth factor needed in order to stimulate tissue growth to a detectable degree. Tissue, in this context, includes connective tissue, bone, cartilage, epidermis and dermis, blood, and other tissues. The actual amount which is determined to be an effective amount will vary depending on factors such as the size, condition, sex and age of the patient and can be more readily determined by the caregiver.

The term "sufficient amount" as used herein is applied to the amount of carrier used in combination with the collagen-polymer conjugates used in forming the strings of the invention. A sufficient amount is that amount which, when mixed with the conjugate, renders it in the physical form desired, for example, extrudable tubes, extrudable cylinders having any desired cross-section, and so forth. Extrudable formulations may include an amount of a carrier sufficient to render the composition smoothly extrudable without significant need to interrupt the extraction process. The amount of the carrier can be varied and adjusted depending on the size and shape of the string being extruded. Such adjustments will be apparent to those skilled in the art upon reading this disclosure.

The term "suitable fibrous material", as used herein, refers to a fibrous material which is substantially insoluble in water, non-immunogenic, biocompatible, and capable of being combined and/or integrated or connected to the strings of the invention. The fibrous material may comprise a variety of materials having these characteristics and are combined with the strings in order to form and/or provide structural integrity for tissue augmentation and/or sutures. For example, the strings extruded with one or more threads which are embedded in the string or the string is woven into the "suitable fibrous material", which can then be wrapped around a bone to provide structural integrity to the bone. Thus, the "suitable fibrous material" is useful in forming the different embodiments of the invention.

The term "in situ" as used herein means at the site of administration. Dehydrated strings are injected or otherwise applied to a site in need of augmentation, and allowed to hydrate and expand at the site of injection. Suitable sites will generally be intradermal or subcutaneous regions for augmenting dermal support, and at the site of a wound being closed with sutures.

The term "aqueous mixture" of collagen includes liquid solutions, suspensions, dispersions, colloids, and the like containing collagen and water.

The term "string" is used herein in an unconventional sense to describe the general dimensions of the objects produced with the collagen/polymer conjugates disclosed herein. In general, a "string" of collagen/polymer conjugates has a shape similar to a conventional string which is a line of material, usually threads, connected together so as to form a narrow elongated cylinder. The collagen/polymer conjugate material used herein can be extruded in any length and in a variety of cross-sectional shapes. However, the "string" is generally extruded in a length of about 1 cm to 100 m, more preferably 5 cm to 10 cm and has a generally circular diameter of about 0.1 mm to about 20 mm, more preferably 0.5 mm to about 2.0 mm. When manufacturing a "string" of the invention, the material is generally extruded in lengths of more than 1 cm, and on a commercial scale, generally longer than 1 m and thereafter cut into appropriate sizes. For example, an extruded string can be cut into lengths of 10 to 20 mm and inserted as a whole or cut into small pieces of about 0.5 to 5 mm in length and inserted as pieces.

The term "dehydrated" means the string is airdried or lyophilized to remove substantially all unbound water.

The term "flexible" means the dehydrated string can be easily bent 90° or more without breaking.

The term "NFC cartilage" as used herein refers to a composition of the invention which resembles cartilage in physical consistency. NFC cartilage is prepared from nonfibrillar collagen (e.g., collagen in solution) and is crosslinked with a hydrophilic polymer, especially using dPEG. As an artifact of the production process or by design, NFC cartilage may contain about 0–20% fibrillar collagen. NFC cartilage is generally prepared by adding dPEG in acidic solution to an acidic solution of collagen, and allowing conjugation to occur prior to neutralization. The term "NFC-FC cartilage" refers to a composition similar to NFC cartilage, wherein the percentage of fibrillar collagen is about 20–80%. NFC-FC cartilage is generally prepared by adding dPEG in a neutralizing buffer to an acidic solution of collagen. The neutralizing buffer causes collagen fibril formation during the conjugation process. Similarly, "FC cartilage" refers to a composition of the invention which is prepared from fibrillar collagen and a difunctional hydrophilic polymer. FC cartilage may generally be prepared using dPEG and fibrillar collagen in neutral solutions/suspensions.

GENERAL METHOD

B.1 Preparation

Extruded Strings

A variety of different collagen-polymer conjugate formulations can be prepared as described below. The formulations are extruded through any suitable orifice including a needle or the nozzle of an extruder device using extrusion technology known to those skilled in the art. The strings of the invention may be extruded in any desired shape or size. The strings are generally circular in cross-section but may have any cross-sectional shape, including oval, square, triangular, hexagonal, etc. The string can be extruded in any length (e.g., about 1 cm to 100 m, preferably 5 cm to about 10 cm) and may have a diameter in the range of about 0.10 mm to 20 mm, preferably 0.5 mm to 2.0 mm.

In accordance With the simplest method of production, the strings are produced by mixing a synthetic hydrophilic polymer with collagen and, within a relatively short period of time (preferably less than 5 minutes), forming that material into a string-like shape. The formation can be carried out by extruding the material or by placing the material within a cast. The extrusion and casting should take place in a relatively short period of time so that it takes place prior to substantial crosslinking.

As a matter of convenience and of manufacturing efficiency, the strings of the invention are generally produced in long lengths exceeding 1 m. After the string is produced, it may be cut into any size appropriate for later use. It is an important feature of the invention that the size of the string can be easily adjusted by the caregiver, depending upon the needs of the patient being treated. For example, if tissue augmentation is believed to require a volume of material which would be filled by 10 mm of string after rehydration, then the string is cut to 10 mm and inserted. If twice that much or half that much volume is required, the size of the string can be adjusted accordingly. When the string is being woven or knitted into a different form, the length of the string is generally greater than 2 cm. Further, when the string is used as an artificial tendon or artificial ligament, it is generally used as a singular piece. However, when the string is used for soft tissue augmentation, the string may be cut into very small pieces on the order of 0.5 to 5 mm and thereafter suspended in a pharmaceutically acceptable nonaqueous carrier and injected, using a syringe, in order to bring about soft tissue augmentation in the desired area. By cutting the string into small pieces, the amount of string injected can be closely controlled in order to closely regulate the amount of augmentation of the soft tissue.

Collagen-polymer strings can also be produced by extruding a cylinder of collagen into a bath containing crosslinker solution. Diffusion of crosslinker occurs from the outside to the center of the string. The amount of time needed to complete the crosslinking reaction varies with the diameter of the string and the concentration of crosslinker used.

In a preferred embodiment, a pharmaceutically acceptable collagen such as Zyderm®I Collagen or Zyderm®II Collagen is mixed with difunctional S-PEG, followed immediately by casting the mixture into narrow bore tubing. The mixture is allowed to gel or polymerize, thereby forming the covalent bonds between the polymer and the collagen. After the polymerization occurs, the structure of the string having a circular cross-section is set and the string can be air-dried to yield a string having a substantially smaller diameter as compared with a string in the hydrated state. Such strings are useful in the formation of a number of different types of biomaterials such as tendons, ligaments, various woven and non-woven structures and sutures. Such strings can also be threaded into fine needles and used for dermal augmentation. When dermal augmentation is the final use, the re-swelling of the dried collagen/S-PEG string provides a variety of benefits.

The present inventors have produced strings by mixing commercially available collagen with difunctionally activated S-PEG in a PBS solution for one to two minutes. After thorough mixing had taken place the material was injected from a syringe using an 18 gauge (or smaller bore) needle into the fine bore of tubing made of a material having poor wettability such as Teflon®. After the material was injected into the Teflon® coated tubing, the ends of the tube were sealed off to prevent desiccation and the tube was incubated at a temperature in the range of 35–40° C. for approximately 12 hours to allow polymerization to be completed, thereby forming the covalent bonds between the collagen and the hydrophilic polymer. Thereafter, the polymerized string was removed from the tubing and the ends of the string were clamped so that the string was freely suspended in air. The string was allowed to dry and the dry material was a substantially straight, fairly stiff, dried collagen thread comprising collagen covalently bound to difunctionally activated succinimidyl polyethylene glycol (dS-PEG).

It will be recognized by those skilled in the art that certain technical modifications will be necessary in order to optimize parameters useful in extruding strings from commercial extrusion devices. However, the details of such can be readily deduced by those skilled in the art based on the disclosure provided herein. To provide assistance in connection with optimizing various parameters, the following information is provided which information was found to be useful in connection with producing the strings on a laboratory useful scale.

Firstly, the total processing time from the mixing of the collagen with the polymer should be kept at under 5 minutes when the temperature is within the range of about 18° C. to 25° C. (room temperature) in order to avoid substantial cross-linking prior to extrusion or casting of the material. Thus, the polymer and collagen should be mixed thoroughly together and extruded or injected into a cast within 5 minutes. If additional processing time is required, the temperature can be reduced in order to reduce the rate of the cross-linking reaction.

When the mixture of polymer and collagen is cast into tubing, it is preferably cast into tubing having its internal surface coated with a non-wettable material which is designed to reduce sticking, such as Teflon ®. Tubing having a non-wettable inner surface is easier to inject into, and longer strings may be produced. If the cast or tubing is small in length and/or the bore of the tubing is large, the string may be extruded out of the cast using hydraulic or air pressure. If extrusion is not possible using pressure, the tubing can be cut. Since cutting the tubing may be necessary, it is desirable to use tubing which includes perforations along the axial line of the tubing. The perforations should be on the outside wall only and not extend into the internal surface diameter of the tubing. Such tubing will readily tear apart along the line of perforation.

As indicated above, it is possible to use fibrillar or nonfibrillar collagen to form the strings of the invention. However, fibrillar collagen is preferred. When the mixture of collagen and polymer is injected into a narrow bore tubing prior to gelation or extruded from the orifice of an extrusion device, the fibers tend to orient along the axis of the tubing. This orientation is believed to impart additional tensile strength to the dried strings. The size of the orifice of the extrusion device and/or the internal diameter of the tubing bore will dictate the maximum diameter of the string being produced. However, the string tends to shrink substantially upon drying and such should be taken into consideration with respect to producing strings of desired thickness and strength.

Prior to casting or extrusion from the orifice of an extrusion device, it is important to remove any air bubbles from the mixture, i.e., carry out de-aeration. If air bubbles are trapped in the mixture, the bubbles will appear in the string as breaks or weakened portions. In order to increase strength, it is also desirable to wash the gel after cross-linking occurs in order to remove dissolved salts and unreacted components.

After a string is formed and polymerization has been completed, the string must be dried. Drying can take place in a variety of different ways. For example, the string can be placed on a flat surface and exposed to the ambient air and/or heat. Such a procedure tends to result in the flattening of the string on the surface which the string is placed on. The upper surface may also be flat, resulting in a ribbon-like or rectangular cross-sectional string. When the string is dried with one end clamped and the other end freely hanging, the freely hanging end dries randomly. Further, there is considerable overall shrinkage in the length of the string and the final dried product is generally not straight. The free end is often jagged or wavy, but becomes straighter towards the attached end. Overall, such strings are weak and easily breakable. If both ends of the string are clamped, the string tends to dry radially and not axially which results in predictable, controlled drying. Further, the length of the string is substantially maintained and the resulting string is substantially straight. A similar effect can be obtained by attaching one end of the string and allowing the other end to hang downward and attaching a small weight at the hanging end.

In general, the string shape is preferably straight for use in soft tissue augmentation and sutures. However, coils or helixes can be produced by wrapping the string around a small diameter rod and allowing the string to dry. Such a procedure will result in a spring-like material which has a certain degree of resilience. Alternatively, the collagen-polymer solution can be injected into coil-shaped hollow tubing to produce a very uniform coil shape. Better control of the drying process can be achieved by drying the strings in an environmental chamber.

As described in Example 10, collagen-polymer strings dried in a coil shape can be pulled straight to facilitate delivery through a needle or catheter, and will then return to their original coil shape upon rehydration in situ. The dried collagen polymer coils may be delivered, in either their straight or coiled shape, through a catheter to the site of an aneurysm. Once in place, the strings will rehydrate to their coil shape and expand to fill the aneurysm.

Conjugates

To form the conjugates used to make the strings of the invention collagen must be chemically bound to a synthetic hydrophilic polymer. This can be carried out in a variety of ways. In accordance with the preferred method, the synthetic hydrophilic polymer is activated and then reacted with the collagen. Alternatively, the hydroxyl or amino groups present on the collagen can be activated and the activated groups will react with the polymer to form the conjugate. In accordance with a less preferred method, a linking group with activated hydroxyl or amino groups thereon can be combined with the polymer and collagen in a manner so as to concurrently react with both the polymer and collagen forming the conjugate. Other methods of forming the conjugates will become apparent to those skilled in the art upon reading this disclosure. Since the conjugates of the invention are to be used in the human body it is important that all of the components, including the polymer, collagen, and linking group, if used form a conjugate that is unlikely to be rejected by the body. Accordingly, toxic and/or immunoreactive components are not preferred as starting materials. Some preferred starting materials and methods of forming conjugates are described further below.

Although different hydrophilic synthetic polymers can be used in connection with forming the conjugate, such polymers must be biocompatible, relatively insoluble, but hydrophilic and is preferably one or more forms of polyethylene glycol (PEG), due to its known biocompatibility. Various forms of PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Further, PEG is generally non-biodegradable and is easily excreted from most living organisms including humans.

The first step in forming the collagen-polymer conjugates generally involves the functionalization of the PEG molecule. Various functionalized polyethylene glycols have been used effectively in fields such as protein modification (see Abuchowski et al., *Enzymes as Drugs,* John Wiley & Sons: New York, N.Y. (1981) pp.

367-383; and Dreborg et al., *Crit. Rev. Therap. Drug Carrier Syst.* (1990) 6:315, both of which are incorporated herein by reference), peptide chemistry (see Mutter et al., *The Peptides,* Academic: New York, N.Y. 2:285-332; and Zalipsky et al., *Int. J. Peptide Protein Res.* (1987) 30:740, both of which are incorporated herein by reference), and the synthesis of polymeric drugs (see Zalipsky et al., *Eur. Polym. J.* (1983) 19:1177; and Ouchi et al., *J. Macromol. Sci. -Chem.* (1987) A24:1011, both of which are incorporated herein by reference). Various types of conjugates formed by the binding of polyethylene glycol with specific pharmaceutically active proteins have been disclosed and found to have useful medical applications in part due to the stability of such conjugates with respect to proteolytic digestion, reduced immunogenicity and longer half-lives within living organisms.

One form of polyethylene glycol which has been found to be particularly useful is monomethoxypolyethylene glycol (mPEG), which can be activated by the addition of a compound such as cyanuric chloride, then coupled to a protein (see Abuchowski et al., *J. Biol. Chem.* (1977) 252:3578, which is incorporated herein by reference). Although such methods of activating polyethylene glycol can be used in connection with the present invention, they are not particularly desirable in that the cyanuric chloride is relatively toxic and must be completely removed from any resulting product in order to provide a pharmaceutically acceptable composition.

Activated forms of PEG can be made from reactants which can be purchased commercially. One form of activated PEG which has been found to be particularly useful in connection with the present invention is mPEG-succinate-N-hydroxysuccinimide ester (SS-PEG) (see Abuchowski et al., *Cancer Biochem. Biphys.* (1984) 7:175, which is incorporated herein by reference). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131, both of which are incorporated herein by reference).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991) incorporated herein by reference to disclose the chemistry involved in linking various forms of PEG to specific biologically active proteins). The stability of urethane linkages has been demonstrated under physiological conditions (see Veronese et al., *Appl. Biochem. Biotechnol.* (1985) 11:141; and Larwood et al., *J. Labelled Compounds Radiopharm.* (1984) 21:603, both of which are incorporated herein by reference). Another means of attaching the PEG to a protein can be by means of a carbamate linkage (see Beauchamp et al., *Anal. Biochem.* (1983) 131:25; and Berger et al., *Blood* (1988) 71:1641, both of which are incorporated herein by reference). The carbamate linkage is created by the use of carbonyldiimidazole-activated PEG. Although such linkages have advantages, the reactions are relatively slow and may take 2 to 3 days to complete.

The various means of activating PEG described above and publications (all of which are incorporated herein by reference) cited in connection with the activation means are described in connection with linking the PEG to specific biologically active proteins and not collagen. However, the present invention now discloses that such activated PEG compounds can be used in connection with the formation of collagen-PEG conjugates. Such conjugates provide a range of improved characteristics and as such can be used to form the various compositions used in forming the strings of the present invention. [*Polymeric Drug and Drug Delivery Systems,* Chapter 10, "Succinimidyl Carbonates of Polyethylene Glycol" (1991), incorporated herein by reference to disclose the chemistry involved in linking various forms of PEG to specific biologically active proteins.]

B.2 Specific Forms of Activated PEG.

As indicated above, the conjugates used in forming the strings can be prepared by covalently binding a variety of different types of synthetic hydrophilic polymers to collagen. However, because the final product or conjugate obtained must have a number of required characteristics such as being extrudable from a nozzle, biocompatible and non-immunogenic, it has been found useful to use polyethylene glycol as the synthetic hydrophilic polymer. The polyethylene glycol must be modified in order to provide activated groups on one or preferably both ends of the molecule so that covalent binding can occur between the PEG and the collagen. Some specific functionalized forms of PEG are shown structurally below, as are the products obtained by reacting these functionalized forms of PEG with collagen.

The first functionalized PEG is difunctionalized PEG succinimidyl glutarate, referred to herein as (SG-PEG). The structural formula of this molecule and the reaction product obtained by reacting it with collagen is shown in Formula 1.

S-PEG: Difunctional PEG Succinimidyl Glutarate

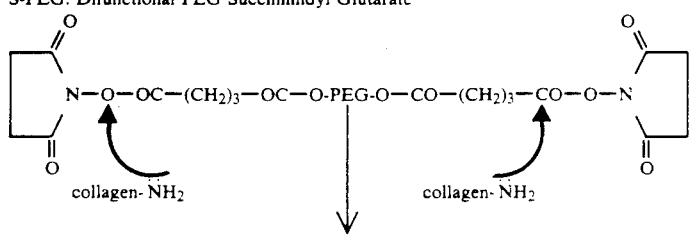

collagen-HN—OC—(CH$_2$)$_3$—OC—O-PEG-O—CO—(CH$_2$)$_3$—CO—NH-collagen    FORMULA 1

Another difunctionally activated form of PEG is referred to as dPEG succinimidyl (dS-PEG). The structural formula for this compound and the reaction product obtained by reacting it with collagen is shown in Formula 2. In a general structural formula for the compound of Formula 2, the subscript 3 is replaced with an "n." In the embodiment shown in Formula 1, n=3, in that there are three repeating CH$_2$ groups on each side of the PEG. The structure in Formula 2 results in a conjugate which includes an "ether" linkage which is not subject to hydrolysis. This is distinct from the first conjugate shown in Formula 1, wherein an ester linkage is provided. The ester linkage is subject to hydrolysis under physiological conditions.

Yet another derivatized form of PEG is provided when n=0. The difunctionalized form is referred to as difunctional PEG succinimidyl carbonate (dSC-PEG). The structural formula of this compound and the conjugate formed by reacting SC-PEG with collagen is shown in Formula 5. Although this conjugate includes a urethane linkage, the conjugate has been found not to have a high degree of stability under physiological conditions. The instability can be a desirable characteristic when the strings are used as sutures in that they dissolve over time as the wound heals.

SC-PEG, n = 0:
Difunctional PEG Succinimidyl Carbonate

S-PEG, n = 3: Difunctional PEG Succinimidyl

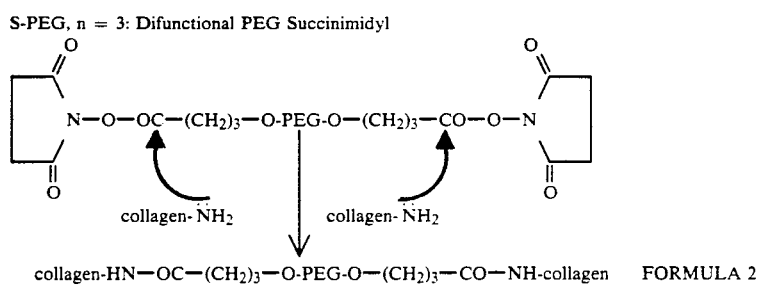

collagen-HN—OC—(CH$_2$)$_3$—O-PEG-O—(CH$_2$)$_3$—CO—NH-collagen    FORMULA 2

Yet another derivatized form of polyethylene glycol, wherein n=2 is shown in Formula 3, as is the conjugate formed by reacting the derivatized PEG with collagen.

S-PEG, n = 2: Difunctional PEG Succinimidyl

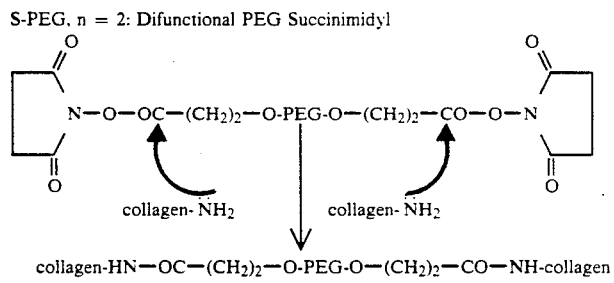

collagen-HN—OC—(CH$_2$)$_2$—O-PEG-O—(CH$_2$)$_2$—CO—NH-collagen

Another preferred embodiment of the invention similar to the compounds of Formula 2 and Formula 3 is provided when n=1. The structural formula and resulting conjugate are shown in Formula 4. It is noted that the conjugate includes both an ether and a peptide linkage. These linkages are stable under physiological conditions.

S-PEG, n = 1: Difunctional PEG Succinimidyl

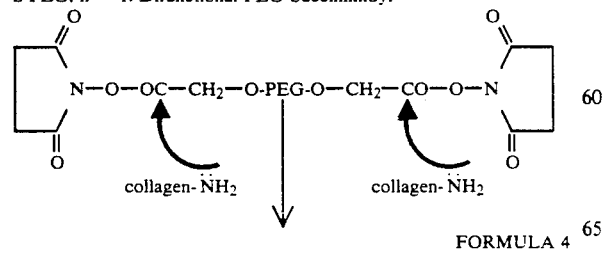

collagen-HN—OC—CH$_2$—O-PEG-O—CH$_2$—CO—NH-collagen

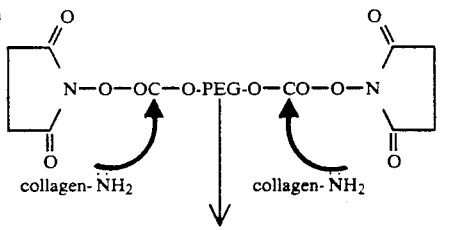

FORMULA 5 collagen-HN—OC—O-PEG-O—CO—NH-collagen

All of the derivatives depicted in Formulas 1-5 involve the inclusion of the succinimidyl group. However, different activating groups can be attached to one or both ends of the PEG. For example, the PEG can be derivatized to form difunctional PEG propion aldehyde (dA-PEG), which is shown in Formula 6, as is the conjugate formed by the reaction of A-PEG with collagen.

A-PEG: Difunctional PEG Propion Aldehyde

FORMULA 4

-continued

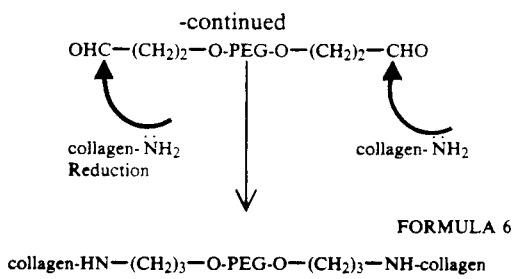

FORMULA 6

Yet another functionalized form of polyethylene glycol is difunctional PEG glycidyl ether (dE-PEG), which is shown in Formula 7, as is the conjugate formed by reacting such with collagen.

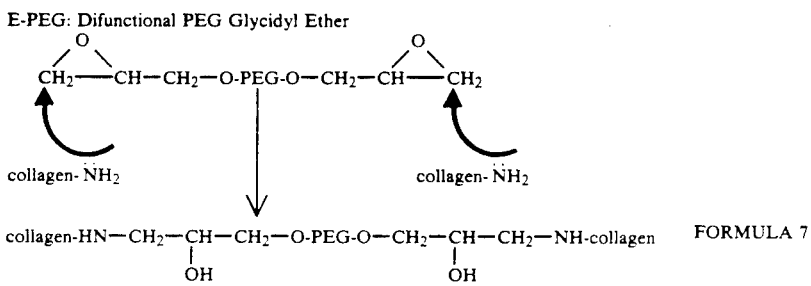

FORMULA 7

The conjugates formed using the functionalized forms of PEG vary depending on the functionalized form of PEG which is used in the reaction. Furthermore, the final product can be varied with respect to its characteristics by changing the molecular weight of the PEG. In general, the stability of the conjugate is improved by eliminating any ester linkages between the PEG and the collagen and including ether and/or urethane linkages. These stable linkages are generally used to form strings for tissue augmentation. When the strings are used as sutures, it may be desirable to include the weaker ester linkages so that the linkages are gradually broken by hydrolysis under physiological conditions, breaking apart the string and releasing a component held therein, such as a growth factor. By varying the chemical structure of the linkage, the rate of sustained release can be varied. Combinations of linkages can be used to produce strings of variable in situ life spans.

Polyfunctional polymers may also be used to crosslink collagen molecules to other proteins (e.g., glycosaminoglycans, chondroitin sulfates, fibronectin, and the like), particularly growth factors, for compositions particularly suited for use in wound healing, osteogenesis, and immune modulation. Such tethering of cytokines to collagen molecules provides an effective slow-release drug delivery system.

Suitable collagens include all types of pharmaceutically useful collagen, preferably types I, II and III. Collagens may be soluble (for example, commercially available Vitrogen ® 100 collagen-in-solution), and may or may not have the telopeptide regions. Preferably, the collagen will be reconstituted fibrillar atelopeptide collagen, for example Zyderm ® collagen implant (ZCI) or atelopeptide collagen in solution (CIS). Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Non-fibrillar, atelopeptide, reconstituted collagen is preferred in order to form strings used for tissue augmentation.

Compositions used in forming the strings of the invention comprise collagen chemically conjugated to a selected synthetic hydrophilic polymer or polymers. Collagen contains a number of available amino and hydroxy groups which may be used to bind the synthetic hydrophilic polymer. The polymer may be bound using a "linking group", as the native hydroxy or amino groups in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'-disuccinimidyl oxalate, N,N'-disuccinimidyl carbonate, and the like. See also Davis, U.S. Pat. No. 4,179,337 for additional linking groups. Presently preferred dicarboxylic anhydrides that are used to form polymer-glutarate compositions include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer composition used to make the strings.

Conjugates with Ester Linkages

In one embodiment, a pharmaceutically pure form of monomethylpolyethylene glycol (mPEG) (mw 5,000) is reacted with glutaric anhydride (pure form) to create mPEG glutarate. The glutarate derivative is then reacted with N-hydroxysuccinimide to form a succinimidyl monomethylpolyethylene glycol glutarate. The succinimidyl ester (mPEG*, denoting the activated PEG intermediate) is then capable of reacting with free amino groups present on collagen (lysine residues) to form a collagen-PEG conjugate wherein one end of the PEG molecule is free or nonbound. Other polymers may be substituted for the monomethyl PEG, as described above. Similarly, the coupling reaction may be carried out using any known method for derivatizing proteins and synthetic polymers. The number of available lysines conjugated may vary from a single residue to 100% of the lysines, preferably 10-50%, and more preferably 20-30%. The number of reactive lysine residues may be determined by standard methods, for example by reaction with TNBS.

The resulting product is a smooth, pliable, rubbery mass having a shiny appearance. It may be wetted, but is not water-soluble. It may be formulated as a suspension at any convenient concentration, preferably about 30-65 mg/mL, and may be extruded through a nozzle to form string. The consistency of the formulation may be adjusted by varying the amount of liquid used.

Conjugate and Cytokines or Growth Factors

Strings can be formed using compositions containing growth factors such as EGF and TGF-$\beta$. The extrudable compositions are prepared by mixing an appropriate amount of the growth factor into the conjugate composition, or by incorporating the cytokine into the collagen prior to treatment with activated PEG. By employing an appropriate amount of difunctional PEG, a degree of crosslinking may be established, along with molecules consisting of collagen linked to a growth factor by a synthetic hydrophilic polymer. Preferably, the cytokine is first reacted with a molar excess of dPEG* in a dilute solution over a 3 to 4 hour period. The cytokine is preferably provided at a concentration of about 1 µg/mL to about 5 mg/mL, while the dPEG* is preferably added to a final concentration providing a 30 to 50-fold molar excess. The resulting conjugated cytokine is then added to an aqueous collagen mixture (about 1 to about 60 mg/mL) at pH 7-8 and allowed to react further. The resulting composition is allowed to stand overnight at ambient temperature.

Membranous Forms

Flexible sheets of material can be prepared by weaving the strings together which sheets can be used directly or in combination with membranous forms of the collagen-polymer conjugate prepared by methods known in the art, for example, U.S. Pat. Nos. 4,600,533; 4,412,947; and 4,242,291. Briefly, high concentration (10-100 mg/mL) CIS or fibrillar collagen (preferably atelopeptide fibrillar collagen, such as ZCI) is cast into a flat sheet container. A solution of mPEG* (having a molecular weight of approximately 5,000) is added to the cast collagen solution, and allowed to react overnight at room temperature. The resulting collagen-polymer conjugate is removed from the reaction solution using a sterile spatula or the like, and washed with PBS to remove excess unreacted mPEG*.

The resulting conjugate may then be compressed under constant pressure to form a uniform, flat sheet or mat, which is then dried to form a membranous implant. More flexible membranous forms are achieved by using lower collagen concentrations and high polymer concentrations as starting materials.

Less flexible membranous forms are prepared by using a dPEG* solution rather than mPEG*. CIS, at room temperature, is mixed with a buffer solution and incubated at 37° C. overnight. The resulting gel is compressed under constant pressure, dried, and desalted by washing. The resultant membrane is then crosslinked by treating with dPEG*, washed, and then dried at low temperature.

Alternatively, CIS or fibrillar collagen (10-100 mg/mL) is cast into a flat sheet container. A solution of dPEG* (22-50% w/v) is added to the cast collagen. The mixture is allowed to react over several hours at room temperature. Shorter reaction times result in more flexible strings and/or membranes. The resulting collagen-polymer membrane may be strengthened with a flexible string of the invention by weaving the string into the member. The string and membrane are dehydrated under a vacuum oven, lyophilization, or air-drying.

B.2 Use and Administration

Strings of the invention have a variety of uses. The strings are suitable for dermal augmentation, for example for filling in dermal creases, and providing support for skin surfaces. The strings can be delivered by any appropriate means including through a needle of appropriate gauge. Such compositions are also useful for augmenting sphincter tissue, (e.g., for restoration of continence). A nonaqueous, pharmaceutically acceptable carrier may additionally be used to aid delivery of the string through a needle. Longer strings may also be mechanically disrupted (e.g., chopped into small pieces) and suspended in a nonaqueous pharmaceutically acceptable carrier for injection. In such cases, the strings are delivered through a fine-gauge needle directly into the sphincter tissue to increase bulk and permit the occluding tissues to meet more easily and efficiently. Articles woven with the strings of the invention may be manually put in place to augment soft tissue or wrapped around a bone and/or bone implant in need of repair or strengthening.

The strings are inserted in a dehydrated form and slowly hydrate and expand several fold in volume (e.g., about 2 to about 7-fold) in situ due to the presence of body fluids. However, the speed of hydration can be increased by injecting an aqueous solution into and around the string. The aqueous solution may be a saline solution or other solution containing salts in concentrations which match the surrounding environment—generally that of human tissue.

Strings or materials woven therefrom may be prepared in a form that is dense and strong enough to substitute for cartilage. These strings and materials are useful for repairing and supporting tissue which require some degree of structure, for example in reconstruction of the nose, ear, knee, larynx, tracheal rings, and joint surfaces.

One or more strings can be woven, knit and/or braided into a flat structure having the desired dimensions necessary to repair and/or replace damaged tendons or ligaments. Alternatively, the strings can be woven, knit and/or braided into a tubular shape and used as a blood vessel graft, vascular stent, nerve graft tube for nerve repair and/or used for the repair and/or replacement of a variety of different channels within a living being.

The overall strength of implants may be substantially increased by weaving, knitting and/or braiding the strings together. Further, the strings can be placed together very closely in a dehydrated state and thereafter allowed to expand upon rehydration in situ which will provide a material which is substantially impermeable and which can be designed to have a relatively smooth service. An important feature of the invention is that the collagen-polymer materials are nonthrombogenic making them highly desirable materials for use in connection with vascular grafts and/or stents and/or any implant which might directly contact blood flow.

When the strings of the invention are used to produce other materials, such as those used in connection with repairing and/or supplementing blood vessels, tendons or ligaments, it is preferable to produce the strings by making an "ether" linkage between the collagen and the polymer. Therefore, linkages such as those shown within Formula 2 should be used. Such linkages are desirable in that the "ether" linkage is not subject to hydrolysis as is an ester linkage. However, in certain situations, it might be desirable to provide a combination of both ester and ether linkage types of materials. The ester linkage materials could be utilized in order to provide for a controlled deterioration and therefore a controlled release of an additional material such as growth factor.

Strings containing cytokines or growth factors are particularly suited for sustained administration of cytokines or growth factors, as in the case of wound healing promotion. Osteoinductive factors and cofactors (including TGF-$\beta$) may advantageously be incorporated into compositions destined for bone repair. Strings may be used to wrap transplanted organs, to suppress rejection and induce improved tissue growth. Alternatively, one may administer antiviral and antitumor factors such as TNF, interferons, CSFs, TGF-$\beta$, and the like for their pharmaceutical activities. The amount of cytokine, growth factor, or other pharmaceutically active drug incorporated in the string will depend upon the severity of the condition being treated, the rate of delivery desired, and the like. However, these parameters may easily be determined by routine experimentation, for example by preparing a model composition following the examples below, forming a string therewith and assaying the release rate in a suitable animal model.

EXAMPLES

The following examples are put forth so as to provide those of ordinary skill in the art with a complete disclosure and description of how to make the conjugates and formulations used to produce the strings and are not intended to limit the scope of what the inventors regard as their invention. Efforts have been made to ensure accuracy with respect to numbers used (e.g. amounts, temperature, molecular weight, etc.) but some experimental errors and deviation should be accounted for. Unless indicated otherwise, parts are parts by weight, molecular weight is average molecular weight, temperature is in degrees Centigrade, and pressure is at or near atmospheric.

EXAMPLE 1

Preparation of Collagen-PEG (A) Monomethyl-PEG 5000 (50 g, 10 mmol, Aldrich Chemical Co.) is dissolved in 1,2-dichoroethane (250 mL) and heated at reflux with glutaric anhydride (5 g) and pyridine (4 mL) under nitrogen for 3 days. The solution is then filtered and the solvent evaporated, and the residue dissolved in water (100 mL) and washed with diethyl ether (2×50 mL). The resulting PEG-glutarate is extracted from the water with chloroform (2×50 mL), and the chloroform evaporated to yield about 43 g of PEG-glutarate. The PEG-glutarate is then dissolved in dimethylformamide (DMF, 200 mL) at 37° C., and N-hydroxysuccinimide (10% molar xs) added. The solution is cooled to 0° C., and an equivalent amount of dicyclohexylcarbodiimide added in DMF solution (10 mL). The mixture is left at room temperature for 24 hours, and then filtered. Cold benzene (100 mL) is then added, and the PEG-succinimidyl glutarate (SG-PEG) precipitated by adding petroleum ether (200 mL) at 0° C. The precipitate is collected on a sintered glass filter. Dissolution in benzene, followed by precipitation with petroleum ether is repeated three times to provide "activated" PEG (SG-PEG).

Vitrogen 100 ® collagen in solution (400 mL, 1.2 g collagen, 0.004 mmol) was mixed with 0.2M phosphate buffer (44 mL) to elevate the pH to 7.4. Next, a threefold molar excess of SG-PEG (6.00 g, 1.2 mmol) was dissolved in water for injection (40 mL) and sterile-filtered. The SG-PEG solution was then added to the collagen solution, and the mixture allowed to stand at 17-22° C. for about 15 hours. The solution was then centrifuged, and the resulting pellet (25 g) of reconstituted fibrils collected and washed with phosphate-buffered saline (PBS, 3×400 mL) to remove residual PEG. The resulting material has a solid, coherent elasticity, and may be picked up on a spatula (the equivalent non-conjugated collagen, Zyderm ® Collagen Implant is more fluid). The resulting material may be extruded or diluted with a sufficient amount of a carrier to allow for the material to be extruded through a nozzle to form a string. The string is dried in order to dehydrate the string for later use.

(B) Similarly, proceeding as in part (A) above but substituting polypropylene glycol and POE-POP block polymers for polyethylene glycol, the corresponding collagen-PPG and collagen-POE-POP compositions are prepared. The compositions may be extruded with or without a diluting carrier to form a string which is then dehydrated.

(C) Difunctionally activated PEG is prepared by dissolving PEG 3400 (34 g, 10 mmol, Aldrich Chemical Co.) in 1,2-dichoroethane (250 mL) and heated at reflux with glutaric anhydride (10 g) and pyridine (4 mL) under nitrogen for 3 days. The solution is then filtered and the solvent evaporated, and the residue dissolved in water (100 mL) and washed with diethyl ether (2×50 mL). The resulting PEG-diglutarate is extracted from the water with chloroform (2×50 mL), and the chloroform evaporated to yield PEG-diglutarate. The PEG-diglutarate is then dissolved in DMF (200 mL) at 37° C., and N-hydroxysuccinimide (10% molar xs) added. The solution is cooled to 0° C., and an equivalent amount of dicyclohexylcarbodiimide added in DMF solution (10 mL). The mixture is left at room temperature for 24 hours, and then filtered. Cold benzene (100 mL) is then added, and the PEG-di(succinimidyl glutarate) (dSG-PEG) precipitated by adding petroleum ether (200 mL) at 0° C. The precipitate is collected on a sintered glass filter. Dissolution in benzene, followed by precipitation with petroleum ether is repeated three times to provide difunctionally "activated" PEG (dPEG*).

Vitrogen 100 ® collagen in solution (400 mL, 1.2 g collagen, 0.004 mmol) was mixed with 0.2M phosphate buffer (44 mL) to elevate the pH to 7.4. Next, a threefold molar excess of dPEG* (6.00 g, 1.2 mmol) was dissolved in water for injection (40 mL) and sterile-filtered. The dPEG* solution was then added to the collagen solution, agitated, and the mixture allowed to stand at 17-22° C. for about 15 hours. The solution was then centrifuged, and the resulting pellet of reconstituted fibrils collected and washed with PBS (3×400 mL) to remove residual dPEG*. The pellet was then placed in a syringe fitted with a Luer lock hub connected to a second syringe, and was passed between the syringes until homogeneous. The resulting material is a microgel or a particulate suspension of random size fibrils in solution (microgel conjugate). The material is a smooth, pliable, rubbery mass, with a shiny appearance. The material may be formed into a string in any appropriate manner and may be diluted, extruded and dried.

EXAMPLE 2

Characterization (A) Collagen-mPEG prepared in Example 1A was characterized and compared with Zyderm ® Collagen Implant (ZCI), and glutaraldehyde-crosslinked fibrillar collagen (GAX).

Extrusion

Tests were carried out to measured the force required to extrude the test composition through a 30 gauge needle. The force required was graphed (in Newtons) versus plunger travel, and ZCI was shown to be extruded smoothly, requiring a force of about 20-30 Newtons. GAX was not extruded smoothly, as shown by a "spiking" exhibited in the force trace. At the plateau, GAX required about 10-15N for extrusion. In contrast, collagen-mPEG demonstrated a very low extrusion force (8-10N), with little or no spiking.

Intrusion

Intrusion is a measure of the tendency of a composition to "finger" or channel into a porous bed, rather than remaining in a compact mass. Low intrusion is preferred in augmentation of soft tissue, so that the injected string does not dissolve and diffuse through the dermis and remains in place.

A 1 mL syringe fitted with a 30 gauge needle was half-filled with silicon carbide particles (60 mesh), simulating human dermis. The upper half of the syringe was filled with 0.5 mL test composition (GAX, ZCI, or collagen-mPEG) at 35 mg/mL. The plunger was then fitted, and depressed. On depression, ZCI appeared at the needle, demonstrating intrusion through the silicon carbide bed. Syringes filled with GAX or collagen-mPEG of the invention did not pass collagen. instead releasing only buffer, demonstrating no intrudability.

Helicity

The portion of each composition exhibiting non-helical character was measured using sensitivity to digestion with trypsin. Samples were treated with the protease trypsin, which is capable of attacking only fragmented portions of the collagen protein. The extent of hydrolysis is measured by fluorescamine assay for solubilized peptides, and the results are expressed as percentage non-helical collagen. The percentage of non-helical collagen was measured 30 minutes after the beginning of the digestion period. The results indicated that ZCI was 3-10% sensitive, GAX was 1-2% sensitive, and collagen-mPEG was about 1% sensitive. Sensitivity to trypsin may also correlate to sensitivity to endogenous proteases following implantation.

Collagenase Sensitivity

The sensitivity of each composition to collagenase was also measured. ZCI was 65.2% digested, compared to 2.2% for GAX, and 45.8% for collagen-mPEG.

Phase Transition

The behavior of each composition versus temperature was examined using a differential scanning calorimeter. On heating, ZCI exhibited multiple peaks at about 45° and 53° C. GAX exhibited a peak at 67-70° C. Collagen-mPEG exhibited a peak at 56-61° C.

Lysine Content

The number of free lysines per mole was determined for each composition using TNBS to quantify reactive epsilon amino groups. ZCI exhibited about 30 lysines per (single helix) molecule (K/m), whereas GAX exhibited 26-27 K/m, and collagen-mPEG 21-26 K/m.

(B) Characterization of Crosslinked Collagen-Polymer Conjugates:

A collagen-dPEG conjugate prepared as described in Example 1C was characterized using differential scanning calorimetry (DSC). This test is a measure of the transition temperature during fragmentation of the collagen molecule at a microscopic level. A lowering of the transition temperature indicates an increase in fragmentation in a manner similar to that measured by trypsin sensitivity.

The collagen-dPEG conjugate showed a single denaturational transition at 56° C. by DSC, which is similar to the typical melting point of the collagen-PEG conjugate prepared in Example 1A. In comparison, ZCI has a melting temperature of 45-53° C. with multiple denaturational transitions, and GAX has a melting temperature of 67-70° C. with a single denaturational transition.

The extrusion test described in Example 2A could not be used to characterize the collagen-dPEG conjugate because the material was not extrudable through a 30 gauge needle.

Using the intrusion test described in Example 2A, the passage of collagen-dPEG was completely blocked at the silicon carbide bed, which indicates high crosslinking between the collagen molecules and little or no intrudability.

EXAMPLE 3

Immunogenicity

Non-crosslinked PEG-Collagen

This experiment was conducted to demonstrate the relative immunogenicity of a collagen-mPEG preparation versus a commercially-available bovine collagen formulation prepared from essentially the same source material, and having a similar consistency. As both collagen preparations were prepared using atelopeptide collagen (which is only weakly immunogenic), the preparations were formulated with either complete Freund's adjuvant (CFA) or incomplete Freund's adjuvant (IFA), to enhance the immune response. This is a severe test, designed to magnify any possible immune reaction.

Collagen-mPEG was prepared as in Example 1A above. Male Hartley guinea pigs (11) were anesthetized and bled by heart puncture for pre-immunization serologic evaluation. Five animals were treated with two 0.1 mL intramuscular injections of Zyderm ® collagen implant (ZCI) emulsified in CFA (1:9) in the left and right thighs. Another five animals were treated in the same fashion, using collagen-PEG (35 mg/mL) emulsified in CFA. One animal was treated with collagen-PEG in IFA. At day 14 following immunization, all animals were again bled by heart puncture, and serum obtained for antibody titer determination (using ELISA). Serology was again performed at day 30.

On day 30, following collection of serum samples, each animal was challenged intradermally with both ZCI and collagen-PEG (0.1 mL of each, one on each flank). Delayed-type hypersensitivity (DTH) was quantified as a measure of cell-mediated immunity. DTH was evaluated at 24, 48, and 72 hours post-challenge by measuring the diameter of any wheal using micrometer calipers, and noting the extent of erythema and induration. Animals were then euthanized with $CO_2$, and the injection sites excised and fixed in neutral, buffered formalin for histological study.

Serological results indicated reduced immunogenicity of collagen-PEG versus ZCI. At day 14, 80% of ZCI immunized animals exhibited "positive" antibody responses (titer≧160 at day 14), whereas 0% of the collagen-PEG immunized animals exhibited positive responses. At day 30, all ZCI-immunized animals exhibited high antibody titers, whereas none of the collagen-PEG-immunized animals (C-PEG) exhibited high titers. The data are shown in Table 1.

TABLE 1

| | Immunogenicity | | |
|---|---|---|---|
| | | Antibody Titer | |
| Animal | Treatment | day 14 | day 30 |
| 1 | ZCI | 320 | >2560 |
| 2 | ZCI | 320 | 1280 |
| 3 | ZCI | 2560 | >2560 |
| 4 | ZCI | 320 | >2560 |
| 5 | ZCI | 80 | 2560 |
| 6 | C-PEG | 0 | 0 |
| 7 | C-PEG | 0 | 160 |
| 8 | C-PEG | 40 | 640 |
| 9 | C-PEG | 0 | 20 |
| 10 | C-PEG | 0 | 640 |
| 11 | C-PEG (IFA) | 0 | 160 |

Responses to the DTH challenge also demonstrated that the collagen-mPEG of the invention is less immunogenic. Guinea pigs immunized with ZCI and challenged with ZCI exhibited a wheal measuring 1.128±0.058 cm in diameter. Animals immunized with collagen-mPEG and challenged with collagen-mPEG exhibited wheals measuring 0.768±0.036 cm. Animals immunized with ZCI and challenged with collagen-mPEG, or immunized with collagen-mPEG and challenged with ZCI, developed wheals smaller than the ZCI-immunized ZCI-challenged wheals. Responses measured at 48 and 72 hours were essentially the same or lower than the 24 hour response for each site. Erythema was essentially the same for all animals.

Histological studies showed that both materials exhibited comparable intrusion, fingering into the dermis and subcutaneous space. Sites of intradermal challenge with ZCI in ZCI-immunized animals exhibited the most extensive inflammatory response, including a cellular infiltrate of lymphohistiocytic elements with eosinophils and occasional giant cells. Two of the implant sites demonstrated an erosive inflammation of the overlying epidermis and eschar formation. Sites of intradermal challenge with collagen-mPEG in ZCI-immunized animals exhibited only a moderate associated inflammatory infiltrate, with a marked reduction in acute cells and lymphoid elements. Histiocytes and giant cells were more prevalent, and in some samples lined and colonized the implants heavily. Animals immunized with collagen-mPEG exhibited only slight to moderate reaction, with ZCI challenge sites accompanied by a modest lymphohistiocytic perivascular infiltrate with a few eosinophils and giant cells. Collagen-mPEG challenge sites were typically accompanied by a minimal scattering of lymphoid cells near the associated vasculature.

EXAMPLE 4

In situ Crosslinking

A dPEG solution was prepared as described in Example 1C above. The following samples were then prepared:

(1) 5 mg dPEG in 80 μL water, mixed with 0.5 mL fibrillar collagen (35 mg/mL), to a final dPEG concentration of 1% by volume;

(2) 15 mg dPEG in 80 μL water, mixed with 0.5 mL fibrillar collagen (35 mg/mL), to a final dPEG concentration of 3% by volume;

(3) Vitrogen ® 100 collagen in solution;

(4) 5 mg dPEG in 80 μL water, mixed with 0.5 mL non-fibrillar collagen (35 mg/mL), to a final dPEG concentration of 1% by volume;

(5) 15 mg dPEG in 80 μL water, mixed with 0.5 mL non-fibrillar collagen (35 mg/mL), to a final dPEG concentration of 3% by volume;

(6) 5 mg dPEG in 0.5 ml PBS, to a final dPEG concentration of 1% by volume; and (7) GAX.

The dPEG solutions of Samples 1, 2, 4, and 5 were placed in a 1 mL syringe equipped with a Luer lock fitting and connector, and joined to another syringe containing the collagen material. The solutions were mixed by passing the liquids back and forth between the syringes several times to form the homogeneous reaction mixture.

The syringe connector was then removed and replaced with a 27 gauge needle, and approximately 50 μL of the reaction mixture was injected intradermally into each of 20 guinea pigs. Samples 3, 6, and 7 were similarly administered through a 27 gauge needle. At intervals up to 30 days following injection, the treatment sites were harvested and studied histologically.

By 30 days, all of the materials appeared to be biocompatible. Samples 1 and 2 displayed wide dispersion with an intermediate degree of interdigitation with dermal collagen fibers. Colonization by connective tissue cells was moderate, and a trace of round cell infiltrate with eosinophils was seen.

Samples 3, 4 and 5 were highly dispersed and finely interdigitated with dermal collagen fibers. Colonization was mild to moderate, and trace levels of round cell infiltration were seen.

Sample 6 had no detectable effects. Sample 7 occurred as large islands with moderate colonization and trace to mild levels of inflammation.

EXAMPLE 5

Extruded Strings

Prepare a collagen-dPEG reaction mixture as described in Example 1C above. Allow reactions to go to completion to form the conjugate and complete crosslinking reactions. Separate the resulting composition into a number of equally-measured parts and add measured amounts of water to each with mixing. Load the resulting mixtures into an extruder and extrude. Judge the results to determine the appropriate amount of water to be added. Dehydrate the extruded string.

EXAMPLE 6

Collagen-Polymer-Growth Factor Conjugates (A) A conjugate containing crosslinked collagen-dPEG-TGF-$\beta$2 was prepared as follows:

A solution of TGF-$\beta$2 and $^{125}$I-TGF-$\beta$2 ($10^5$ cpm; 25 $\mu$L of 1 mg/mL) was added to a solution of dPEG* (4 mg) in $CH_2Cl_2$ (100 $\mu$L), and the mixture allowed to react for 12 (sample #3) or 35 (sample #5) minutes at 17° C. To this was added 2.5 mL of collagen solution (3 mg/mL atelopeptide nonfibrillar collagen), and the resulting mixture allowed to incubate overnight at ambient temperature. The pellet which formed was collected by centrifugation to provide collagen-dPEG-TGF-$\beta$2.

(B) A composition based on fibrillar atelopeptide collagen was prepared as in part A above, but limiting TGF-$\beta$2/dPEG* reaction time to 2 minutes, and substituting 7 mg of fibrillar collagen (precipitated from collagen in solution within 2 minutes prior to use) for collagen in solution.

(C) A composition containing dPEG-crosslinked collagen and free TGF-$\beta$2 was prepared as follows:

A solution of dPEG* (4 mg) in $CH_2Cl_2$ (100 $\mu$L), was added to 2.5 mL of CIS (3 mg/mL atelopeptide nonfibrillar collagen), and the resulting mixture allowed to incubate overnight at ambient temperature. The pellet which formed was washed to remove unreacted dPEG*, and 25 $\mu$g of TGF-$\beta$2 mixed in to provide collagen-dPEG+TGF-$\beta$2.

(D) The degree of TGF-$\beta$2 binding was determined as follows:

Each composition prepared in parts A-C above was washed six times with 0.5 mL of buffer (0.02M phosphate buffer, 0.1% BSA) by vigorous vortexing followed by centrifugation in order to remove non-bound TGF-$\beta$2. The pellet and supernatants were collected at each time of washing, and were counted. The TGF-$\beta$2 in the simple mixture is quantitatively released within about 6 washings, while approximately 40% of the TGF-$\beta$2 is retained in the compositions of part B and 50% is retained in the compositions of part A.

(E) The biological activity of the materials prepared above was assayed as follows:

Compositions prepared according to part A (CIS-dPEG-TGF-$\beta$2) (TGF-$\beta$2/dPEG* reaction time of 12 minutes) and part C (CIS-dPEG+TGF-$\beta$2) were prepared, as well as a control prepared according to part C without TGF-$\beta$2 (CIS-dPEG). The samples were washed in PBS/BSA eight times then washed an additional three times in fetal bovine serum (Gibco) at 37° C. This washing protocol resulted in visually detectable material loss, so remaining TGF-$\beta$2 content was determined by counting the remaining $^{125}$I TGF-$\beta$2 activity was then assayed by ELISA. The results are shown in Table 2 below.

TABLE Z

Retention of Biological Activity

| Sample | $^{125}I$ Counts | remaining TGF-$\beta$2($\mu$g) | O.D. (414 nm) |
|---|---|---|---|
| CIS-dPEG | 0 | 0 | 0.015 |
| | | | 0.015 |
| CIS-dPEG + TGF-$\beta$2 | 2775 | 0.5-1.0 | 0.029 |
| | | | 0.035 |
| CIS-dPEG-TGF-$\beta$2 | 42604 | 7.4 | 0.102 |
| | | | 0.082 |

The data demonstrates that the TGF-$\beta$1 retained in the compositions of the invention remains in a substantially active form.

EXAMPLE 7

Formulations (A) A formulation suitable for extrusion were prepared by suspending collagen-PEG in sterile water for injection, at 35 mg/mL. The characteristics of the resulting formulation are described in Example 2 above.

(B) A formulation useful for repair of stress-bearing bone defects (e.g., fractures, nonunions, and the like) may be prepared by mixing collagen-PEG of the invention with a suitable particulate, insoluble component. The insoluble component may be fibrillar crosslinked collagen, gelatin beads, polytetrafluoroethylene beads, silicone rubber beads, hydrogel beads, silicon carbide beads, mineral beads, or glass beads, and is preferably a calcium mineral, for example hydroxyapatite and/or tricalcium phosphate.

Solid formulations were prepared by mixing Zyderm®II (65 mg/mL collagen) or collagen-mPEG (63 mg/mL) with particulate hydroxyapatite and tricalcium phosphate (HA+TCP) and air drying to form a solid block containing 65% HA by weight. Optionally, blocks were heat-treated by heating at 75° C. for 10 hours. The resulting blocks were hydrated in 0.13M saline for 12 hours prior to testing.

On standing, it was observed that Zyderm®-HA+TCP (Z-HA) compositions separated into three phases, whereas PEG-collagen-HA+TCP (PC-HA) compositions remained single phase.

Each block was elongated by 5%, and its stress relaxation monitored for 1 minute after release. After this test, each block was subjected to constant elongation at a constant 1 cm/min until failure. The results are shown in Table 3:

TABLE 3

| | Mechanical Strength | | | | |
|---|---|---|---|---|---|
| | Stress Relaxation | | | Constant Extension | |
| Sample | Peak Force | Constant Force | $t_{\frac{1}{2}}$ (min) | Rupture Force | Extension at Rupture |
| Z-HA | 1.5 | 1.1 | 0.04 | 2.6 | 11.0% |
| (air) | — | — | — | 2.6 | 15.3% |
| Z-HA | 1.5 | 1.1 | 0.06 | — | — |
| (heat) | 1.4 | 1.0 | 0.07 | 3.4 | 14.0% |
| PC-HA | 2.6 | 1.8 | 0.06 | 5.5 | 12.3% |
| (air) | 2.8 | 2.1 | 0.08 | 5.4 | 11.7% |
| PC-HA | 3.3 | 2.6 | 0.04 | 5.4 | 12.0% |
| (heat) | 3.6 | 2.7 | 0.06 | 5.4 | 20.3% |

All forces reported in newtons. Extension at rupture (strain) reported in percent extension.

The data demonstrate that collagen-polymer forms HA+TCP compositions exhibiting substantially greater tensile strength. Thus, one can prepare implant compositions with collagen-polymer which are substantially stronger than compositions employing the same amount of non-conjugated collagen, or may reduce the amount of collagen-polymer employed to form a composition of equal strength.

EXAMPLE 8

A 10% solution of activated difunctional SG-PEG was prepared by diluting 100 mg of powdered difunctional SG-PEG (3400 dalton MW) in 1 ml of phosphate buffered saline (PBS). One (1) ml of the 10% difunctional SG-PEG solution was mixed with 9 ml of Zyderm®I Collagen (Z-I, 35 mg/ml) to achieve a final PEG concentration of 1%. The collagen and crosslinker solution were placed in 10-ml syringes and mixed using syringe-to-syringe mixing.

Zyderm®II Collagen (Z-II, 65 mg/ml) was crosslinked with difunctional SG-PEG using the same method described above.

The syringes containing the Z-I-PEG and Z-II-PEG composites were incubated at 37° C. for 16 hours and formed polymerized gels.

The needle end of each of the two syringes was cut off and the gels pushed out of the barrels of the syringes using the respective syringe plungers. The solid gels were then sliced into disks of 2 mm thickness, dehydrated, and then rehydrated.

Diameter, thickness and weight of the disks were measured in the fresh (wet), dehydrated, and rehydrated states. Results of these measurements are presented in Table 4, below.

ing to ensure that the strings would dry in the radial, rather than axial, dimension.

Non-crosslinked collagen strings were produced as a control by mixing 5 ml of Zyderm®I Collagen with 0.5 ml of PBS. The method described above was used to produce strings of two different diameters.

Diameter, length, and weight of the strings were measured in the fresh (wet), dehydrated, and rehydrated states. Results of these measurements are presented in Table 5 and FIG. 1.

TABLE 5

| Sample* | Swellability of Collagen Strings Crosslinked by dSG-PEG Compared to Non-Crosslinked Collagen Strings | | | | | | | | |
|---|---|---|---|---|---|---|---|---|---|
| | Diameter (mm) | | | Thickness (mm) | | | Weight (grams) | | |
| | Fresh | Dehyd. | Rehyd. | Fresh | Dehyd. | Rehyd. | Fresh | Dehyd. | Rehyd. |
| Z-I | 0.9 | 0.30 | | 30 | 25 | | 0.0158 | 0.0015 | |
| | 2.5 | 0.46 | | 30 | 25 | | 0.129 | 0.0091 | |
| Z-I + PEG | 0.9 | 0.30 | 0.6 | 27 | 24 | 27 | 0.0175 | 0.0012 | 0.0139 |
| | 2.5 | 0.46 | 2.3 | 30 | 22 | 30 | 0.168 | 0.0101 | 0.1395 |

*Z-I = Zyderm® I Collagen

Because the non-crosslinked strings do not contain the hydrophilic PEG, they were not able to take up water and rehydrate. Therefore, no measurements were obtained for these strings in the rehydrated state.

As with the PEG-crosslinked collagen disks described in Example 8, the strings retained all of their original length and nearly all of their original diameter and weight upon rehydration.

TABLE 4

| Sample* | Swellability of Collagen Disks (35 and 65 mg/ml) Crosslinked by dSG-PEG | | | | | | | | |
|---|---|---|---|---|---|---|---|---|---|
| | Diameter (mm) | | | Thickness (mm) | | | Weight (grams) | | |
| | Fresh | Dehyd. | Rehyd. | Fresh | Dehyd. | Rehyd. | Fresh | Dehyd. | Rehyd. |
| Z-I + PEG | 14 | 12 | 13.1 | 2.0 | 0.6 | 1.9 | 0.3213 | 0.0215 | 0.3048 |
| Z-II + PEG | 14 | 10 | 13.7 | 2.0 | 1.0 | 1.8 | 0.4111 | 0.0385 | 0.3943 |

*Z-I = Zyderm® I Collagen
Z-II = Zyderm® II Collagen

The crosslinked collagen disks (at both collagen concentrations) regained nearly all of their original dimensions upon rehydration.

EXAMPLE 9

Five (5) ml of Zyderm®I Collagen (35 mg/ml) was mixed with 50 mg of difunctional SG-PEG in 0.5 ml of phosphate buffered saline (PBS) using syringe-to-syringe mixing. The material was immediately transferred to either 1.5 or 3.5 mm diameter Teflon® tubing, then incubated at 37° C. for 16 hours. The crosslinked collagen gels were removed from the tubing and dried overnight. The strings were held taut during dry- Various rheological measurements were performed on the crosslinked and non-crosslinked strings in their dehydrated states. All strings were cut to a constant length of 20 mm prior to rheological evaluation. Results are presented in Table 6, below. Bar graphs with error bars showing standard deviation for several rheological measurements on each of the four string types are presented in FIGS. 2-5.

TABLE 6

| Sample* | Mechanical Strength of Collagen Strings Crosslinked by dSG-PEG Compared to Non-Crosslinked Collagen Strings | | | | | | |
|---|---|---|---|---|---|---|---|
| | Diameter (mm) | Length (mm) | Tensile Strength (N) | Tensile Stress (N/mm$^2$) | Δ Length (mm) | Strain (ΔL/L) | Young's Modulus (N/mm$^2$) |
| Z-I | 0.30 | 20 | 1.0 | 14.9 | 1.0 | 0.0488 | 305 |
| | | | 2.0 | 30.3 | 1.4 | 0.0676 | 448 |
| | | | 1.0 | 14.9 | 1.0 | 0.0488 | 305 |
| Z-I + PEG | 0.30 | 20 | 6.5 | 127 | 7.7 | 0.3257 | 391 |
| | | | 6.0 | 112 | 6.5 | 0.2814 | 402 |
| | | | 6.5 | 131 | 8.5 | 0.3541 | 370 |
| Z-I | 0.46 | 20 | 18.2 | 121 | 2.0 | 0.0953 | 1264 |
| | | | 24.0 | 160 | 2.2 | 0.1040 | 1537 |
| | | | 8.0 | 51 | 1.2 | 0.0583 | 875 |
| Z-I + PEG | 0.46 | 20 | 29.0 | 223 | 5.5 | 0.2429 | 916 |
| | | | 26.0 | 198 | 5.4 | 0.2390 | 829 |
| | | | 25.5 | 197 | 5.6 | 0.2468 | 796 |

*Z-I = Zyderm® I Collagen

Tensile stress (N/mm$^2$) is a measure of the force at failure (breakage) of the string as a function of its cross-sectional area. Strain (Δ length/length) and Δ length are measures of the elasticity of the string (how much it will stretch under tension). Young's Modulus (N/mm$^2$) is calculated by dividing stress by strain and is known as the rheological "fingerprint" of a particular material.

The bar graphs in FIGS. 2-5 illustrate the large standard deviation and variability of the rheological measurements obtained for the non-crosslinked strings, showing the non-homogeneity of the non-crosslinked materials. The consistent results obtained with the PEG-crosslinked strings show that PEG crosslinking imparts homogeneity, as well as greater mechanical strength and elasticity, to the collagen material.

EXAMPLE 10

Preparation of Coiled Strings

A small-diameter crosslinked collagen string was produced as described in Example 9 by injecting collagen in a 1% solution of difunctional S-PEG through an 18-gauge needle into TFE tubing (0.9 mm outer diameter, 0.6 mm inner diameter).

Following removal from the tubing, the wet string was coiled around a second piece of TFE tubing having an outer diameter of 1.5 mm. The coiled string was dried on the tubing for 2 days at room temperature under the fume hood.

The dehydrated PEG-collagen coil was pushed off the tubing. The coiled string in its dried state was manually pulled straight. The now-straight string was immersed in water and quickly returned to its coiled shape upon rehydration.

The coiled wet string was removed from the water bath, pulled and dried straight under tension. The straight dried string was again immersed in water and again returned to its original coiled shape upon rehydration.

The collagen-polymer coils can be pulled straight to facilitate delivery through a needle or catheter. They are especially useful in the treatment of aneurysms because of their ability to rehydrate to the coil shape and expand to fill the void.

The above example illustrates the "memory" of the collagen-polymer material. Upon rehydration, the material returns to the original shape in which it was first dried.

The invention is shown and described herein at what is considered to be the most practical, and preferred embodiments. It is recognized, however, that departures may be made therefrom which are within the scope of the invention and that obvious modifications will occur to one skilled in the art upon reading this disclosure.

What is claimed:

1. A dehydrated string having a circular cross-section and being in the form of an elongated cylinder and having a diameter in the range of about 0.25 mm to about 2.5 mm, the string comprising collagen chemically conjugated to a synthetic non-immunogenic hydrophilic polymer by a covalent bond and wherein the string is flexible, and wherein the covalent bond is selected from the group consisting of an ester linkage, a urethane linkage, and an ether linkage.

2. The string of claim 1, wherein the synthetic hydrophilic polymer is a difunctionally activated polyethylene glycol.

3. The string of claim 1, wherein the polymer is difunctional polyethylene glycol succinimidyl.

4. The string of claim 1, further comprising:
a therapeutically effective amount of a cytokine or growth factor dispersed homogeneously in the polymer.

5. The string of claim 4, wherein said cytokine or growth factor is selected from the group consisting of epidermal growth factor, transforming growth factor-α, transforming growth factor-β, transforming growth factor-β2, platelet-derived growth factor-AA, platelet-derived growth factor-AB, platelet-derived growth factor-BB, acidic fibroblast growth factor, basic fibroblast growth factor, connective tissue activating peptide, β-thromboglobulin, insulin-like growth factors, tumor necrosis factor, interleukins, colony stimulating factors, erythropoietin, nerve growth factor, interferons, and osteogenic factors.

6. The string of claim 5, wherein said growth factor is selected from the group consisting of transforming growth factor-β, transforming growth factor-β1, transforming growth factor-β2, and erythropoietin.

7. The string of claim 1, wherein the synthetic hydrophilic polymer is a succinimidyl monomethyl-polyethylene glycol glutarate.

8. The string of claim 1, wherein the conjugate has the following general structural formula:

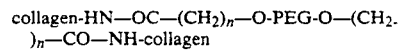

collagen-HN—OC—(CH$_2$)$_n$—O-PEG-O—(CH$_2$)$_n$—CO—NH-collagen wherein n is an integer selected from the group consisting of 0, 1, 2, 3, or 4.

9. The string of claim 1, wherein the collagen is selected from the group consisting of type I, type II and type III collagen and the polymer is polyethylene glycol having a weight average molecular weight of about 100 to about 20,000.

10. The string of claim 1, wherein the synthetic hydrophilic polymer is bound to an available lysine residue on the collagen, and the collagen is atelopeptide fibrillar collagen.

11. The string of claim 1, wherein the covalent bond is an ether linkage.

12. A method of soft tissue augmentation comprising administering into soft tissue a dehydrated and flexible string having a circular cross-section and being in the form of an elongated cylinder having a diameter in the range of about 0.25 mm to about 2.5 mm, the string comprising collagen chemically conjugated to a synthetic non-immunogenic hydrophilic polymer by a covalent bond and wherein the covalent bond is selected from the group consisting of an ester linkage, a urethane linkage, and an ether linkage.

13. The method of claim 12, further comprising;
injecting an aqueous solution into where the string was administered, and wherein the collagen is non-fibrillar collagen.

14. The method of claim 13, wherein the synthetic, hydrophilic, non-immunogenic polymer has a structural formula selected from the group consisting of;

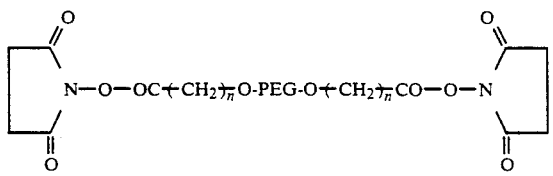

wherein n is selected from the group consisting of 0, 1, 2, 3 and 4;

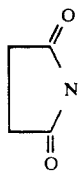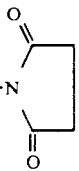

and;

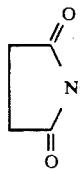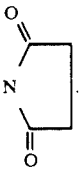

15. The method of claim 12, wherein the covalent bond is an ether linkage.

16. A method of suturing a wound comprising sewing the wound closed with a dehydrated, flexible string having an outer diameter in the range of about 0.10 mm to about 20 mm, and a length of more than 2 cm, the string comprising collagen chemically conjugated to a synthetic, non-immunogenic, hydrophilic polymer by a covalent bond.

17. A material comprised of a woven, knitted, or braided string, wherein the string comprises collagen chemically conjugated to a synthetic hydrophilic polymer by covalent bond, the string having a diameter in the range of 0.10 mm to about 20 mm.

18. The material of claim 17, wherein the material is comprised of a plurality of strings and each of the strings has a diameter in the range of 0.25 mm to about 2.5 mm.

19. The material as claimed in claim 18, wherein the material is woven into the shape of a tube.

20. A method of repairing a channel within a living being comprising attaching to the channel in need of repair a tube as claimed in claim 19.

21. A method of soft tissue augmentation comprising administering into soft tissue a composition comprised of a string having a diameter in the range of about 0.1 mm to about 20 mm, which string has been cut into lengths in the range of 0.5 to 5 mm and thereafter dispersed in a pharmaceutically acceptable non-aqueous carrier, the string comprising collagen chemically conjugated to a synthetic non-immunogenic hydrophilic polymer by a covalent bond.

22. The method of claim 21, wherein the string is flexible, and wherein the covalent bond is selected from the group consisting of an ester linkage, a urethane linkage, and an ether linkage.

23. The method of claim 22, wherein the string is further comprised of a therapeutically effective amount of cytokine or growth factor dispersed homogeneously in the string.

* * * * *